US008659420B2

(12) United States Patent
Salvat, Jr.

(10) Patent No.: US 8,659,420 B2
(45) Date of Patent: Feb. 25, 2014

(54) TRACKING SYSTEM AND DEVICE

(75) Inventor: Roberto Salvat, Jr., Palm Beach Gardens, FL (US)

(73) Assignee: S.I.P. Holdings, LLC, Palm Beach Gardens, FL (US)

( * ) Notice: Subject to any disclaimer, the term of this patent is extended or adjusted under 35 U.S.C. 154(b) by 349 days.

(21) Appl. No.: 12/973,394

(22) Filed: Dec. 20, 2010

(65) Prior Publication Data

US 2011/0227722 A1  Sep. 22, 2011

Related U.S. Application Data

(63) Continuation-in-part of application No. 11/861,858, filed on Sep. 26, 2007, now Pat. No. 7,868,754, and a continuation-in-part of application No. 12/963,309, filed on Dec. 8, 2010, now abandoned.

(51) Int. Cl.
*G08B 1/08* (2006.01)
*G08B 23/00* (2006.01)

(52) U.S. Cl.
USPC .......... 340/539.13; 340/5.92; 340/572.1; 340/572.3; 235/384; 705/22; 705/28

(58) Field of Classification Search
USPC ............ 340/539.13, 5.92; 705/22, 28, 29
See application file for complete search history.

(56) References Cited

U.S. PATENT DOCUMENTS

| | | |
|---|---|---|
| 2,267,263 A | 12/1941 | Berger et al. |
| 2,352,788 A | 7/1944 | Hinds |
| 2,583,990 A | 1/1952 | Baumer |
| 2,588,306 A | 3/1952 | Taylor, Jr. |
| 2,609,105 A | 9/1952 | Weaver |
| 2,816,045 A | 12/1957 | Cooper |
| 5,712,789 A * | 1/1998 | Radican .............. 700/226 |
| 6,490,351 B1 | 12/2002 | Roberts |
| 6,512,478 B1 | 1/2003 | Chien |
| 6,828,908 B2 | 12/2004 | Clark |
| 7,091,266 B2 | 8/2006 | Murakami et al. |
| 7,102,508 B2 | 9/2006 | Edelstein et al. |
| 7,106,189 B2 | 9/2006 | Burneske et al. |
| 7,106,245 B2 | 9/2006 | Komiak et al. |
| 7,113,099 B2 | 9/2006 | Tyroler et al. |
| 7,119,738 B2 | 10/2006 | Bridgelall et al. |
| 7,123,149 B2 | 10/2006 | Nowak et al. |
| 7,136,832 B2 | 11/2006 | Li et al. |

(Continued)

FOREIGN PATENT DOCUMENTS

WO   WO2010025217   3/2010

*Primary Examiner* — Donnie Crosland
(74) *Attorney, Agent, or Firm* — McHale & Slavin, P.A.

(57) ABSTRACT

A tracking device and system for tracking containers, in particular, containers and their contents, is disclosed. The tracking device utilizes AGPS/GPS/GSM/CDMA/LTE/EVDO/WiFi/RFID/Bluetooth®/TDMA technology to enable an individual to locate and monitor the movement of a Container at any given time and for any desired period of time. The tracking system utilizes virtual geo-fences to identify buildings or specific addresses to assist in determining the specific location of the containers in relation to these buildings or specific addresses. The tracking devices can also be activated by motion sensors to alert the tracking system of a possible theft of the container or sudden movement. The tracking system incorporates software which enables an individual to determine the location of the containers, determine the contents of the containers, and schedule the use of the containers by specific persons and at specific locations. The tracking system also retains information regarding the persons, the supplier's representatives, the warehouses and sales of the containers and any contents that they may have.

11 Claims, 29 Drawing Sheets

(56) References Cited

U.S. PATENT DOCUMENTS

| | | |
|---|---|---|
| 7,138,902 B2 | 11/2006 | Menard |
| 7,138,913 B2 | 11/2006 | Mackenzie et al. |
| 7,138,914 B2 | 11/2006 | Culpepper et al. |
| 7,148,800 B2 | 12/2006 | Cunningham et al. |
| 7,154,409 B2 | 12/2006 | Mohammed et al. |
| 7,158,030 B2 | 1/2007 | Chung |
| 7,158,754 B2 | 1/2007 | Anderson |
| 7,164,359 B2 | 1/2007 | Waterhouse et al. |
| 7,171,187 B2 | 1/2007 | Haave et al. |
| 7,253,731 B2 * | 8/2007 | Joao ............ 340/539.13 |
| 7,268,684 B2 | 9/2007 | Tethrake et al. |
| 7,420,468 B2 | 9/2008 | Fabian et al. |
| 7,557,710 B2 | 7/2009 | Sanchez et al. |
| 7,633,393 B2 | 12/2009 | Bonne |
| 7,728,729 B2 | 6/2010 | Christopher |
| 7,860,583 B2 | 12/2010 | Condurso et al. |
| 7,868,754 B2 | 1/2011 | Salvat, Jr. |
| 8,223,009 B2 * | 7/2012 | Anderson et al. ......... 340/539.1 |
| 2002/0067263 A1 | 6/2002 | Tafoya et al. |
| 2002/0133709 A1 | 9/2002 | Hoffman |
| 2003/0052788 A1 | 3/2003 | Chung |
| 2003/0091612 A1 | 5/2003 | Sabesan |
| 2005/0088306 A1 | 4/2005 | Andreasson et al. |
| 2005/0183990 A1 | 8/2005 | Corbett, Jr. |
| 2005/0285740 A1 | 12/2005 | Kubach et al. |
| 2006/0017545 A1 | 1/2006 | Volpi et al. |
| 2006/0043179 A1 | 3/2006 | Nycz et al. |
| 2006/0093744 A9 | 5/2006 | Suzuki et al. |
| 2006/0109105 A1 | 5/2006 | Varner et al. |
| 2006/0145871 A1 | 7/2006 | Donati et al. |
| 2007/0001809 A1 | 1/2007 | Kodukula et al. |
| 2007/0028642 A1 | 2/2007 | Glade et al. |
| 2007/0160494 A1 | 7/2007 | Sands |
| 2007/0222122 A1 | 9/2007 | Ong et al. |
| 2008/0030345 A1 | 2/2008 | Austin et al. |
| 2008/0150722 A1 | 6/2008 | Jackson |
| 2008/0157970 A1 | 7/2008 | Single et al. |
| 2008/0316045 A1 | 12/2008 | Sriharto et al. |
| 2011/0077024 A1 | 3/2011 | Salvat, Jr. |

* cited by examiner

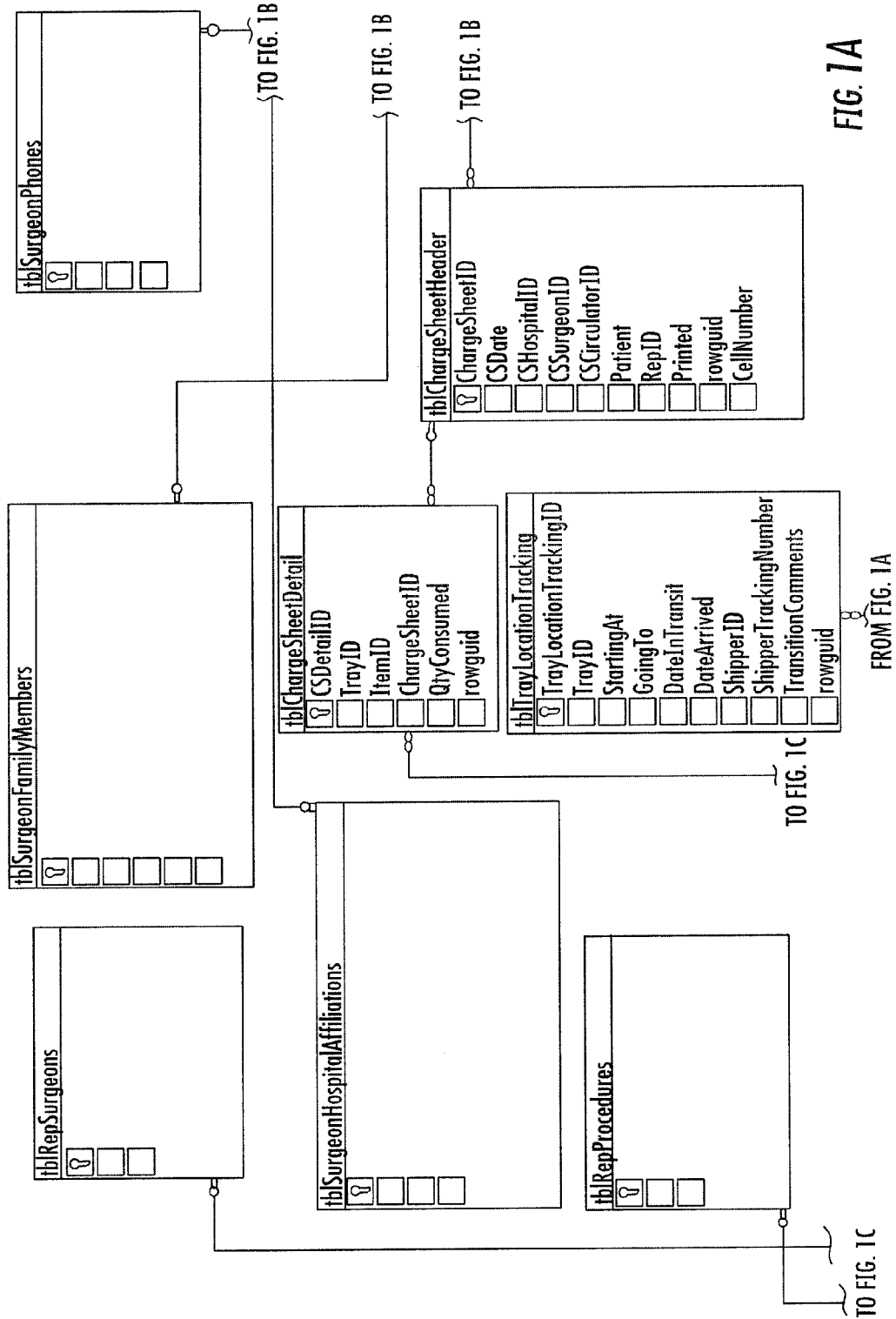

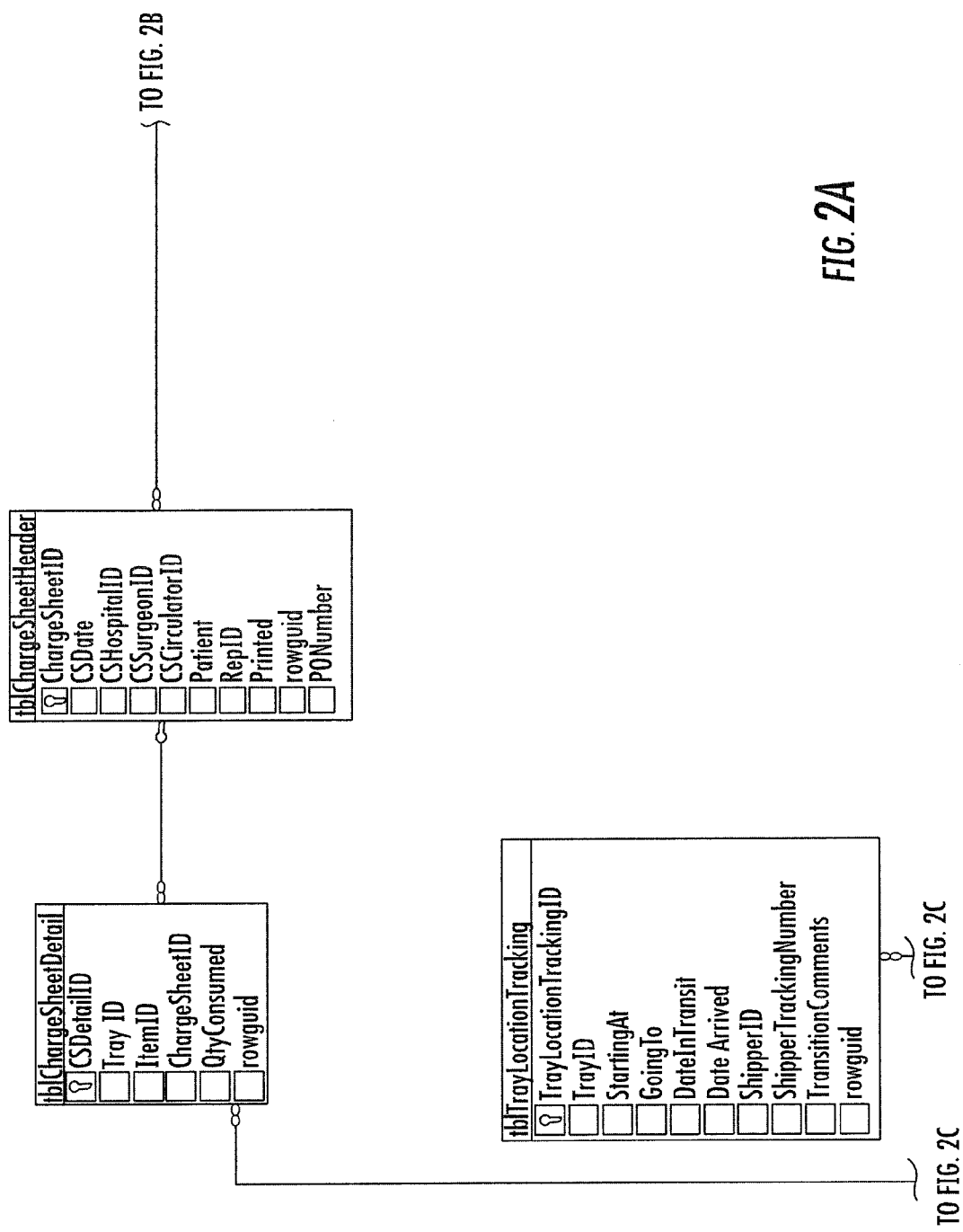

XYZ Backoffice - WINDOWS INTERNET EXPLORER http://backoffice.XYZ.com/AssignTraySurgicalOrders.asp

File  Edit  View  Favorites  Tools  Help

TRAY AVAILABILITY
TOTAL RECORDS: 124

| TRAY NUMBER | TRAY TYPE | CURRENTLY AT | DATE DUE | DATE AVAILABLE AFTER USE | NEED FOR SURGERY AT | SURGERY DATE | TRAY ID |
|---|---|---|---|---|---|---|---|
| 1112223 | ANTERIOR GENERAL INSTRUMENT TRAY | GWINNETT MEDICAL | 8/15/2007 | 8/17/2007 | NORTHSIDE HOSPITAL | 8/17/2007 | 20 |
| 1112223 | ANTERIOR GENERAL INSTRUMENT TRAY | GWINNETT MEDICAL | 8/3/2007 | 8/5/2007 | ST JOSEPHS OF ATLANTA | 8/15/2007 | 20 |
| 1112223 | ANTERIOR GENERAL INSTRUMENT TRAY | GWINNETT MEDICAL | 9/18/2007 | 9/20/2007 | NORTH HOSPITAL | 9/20/2007 | 20 |
| 11235 | ANTERIOR GENERAL INSTRUMENT TRAY | GRADY HOSPITAL | 8/8/2007 | 8/10/2007 | GRADY HOSPITAL | 8/10/2007 | 21 |
| 11235 | ANTERIOR GENERAL INSTRUMENT TRAY | GRADY HOSPITAL | 8/11/2007 | 8/13/2007 | GRADY HOSPITAL | 8/17/2007 | 21 |
| 11235 | ANTERIOR GENERAL INSTRUMENT TRAY | GRADY HOSPITAL | 8/29/2007 | 8/31/2007 | GRADY HOSPITAL | 8/31/2007 | 21 |
| 11235 | ANTERIOR GENERAL INSTRUMENT TRAY | GRADY HOSPITAL | 8/11/2007 | 8/13/2007 | GRADY HOSPITAL | 8/20/2007 | 21 |
| 11235 | ANTERIOR GENERAL INSTRUMENT TRAY | GRADY HOSPITAL | 8/13/2007 | 8/15/2007 | GRADY HOSPITAL | 8/15/2007 | 21 |
| 11235 | ANTERIOR GENERAL INSTRUMENT TRAY | GRADY HOSPITAL | 8/29/2007 | 8/26/2007 | GRADY HOSPITAL | 8/26/2007 | 21 |
| 11235 | ANTERIOR GENERAL INSTRUMENT TRAY | GRADY HOSPITAL | 8/29/2007 | 8/31/2007 | GRADY HOSPITAL | 8/31/2007 | 21 |
| 99887745 | CERVICAL ALLOGRAFT TRAY | GRADY HOSPITAL | 8/8/2007 | 8/10/2007 | GWINNETT MEDICAL | 8/9/2007 | 17 |
| 99887745 | CERVICAL ALLOGRAFT TRAY | GRADY HOSPITAL | 9/2/2007 | 9/4/2007 | NORTH FULTON HOSPITAL | 9/4/2007 | 17 |
| 99887745 | CERVICAL ALLOGRAFT TRAY | GRADY HOSPITAL | 9/4/2007 | 9/6/2007 | NORTH FULTON HOSPITAL | 9/6/2007 | 17 |
| 99887745 | CERVICAL ALLOGRAFT TRAY | GRADY HOSPITAL | 9/9/2007 | 9/11/2007 | NORTH FULTON HOSPITAL | 9/11/2007 | 17 |
| 99887745 | CERVICAL ALLOGRAFT TRAY | GRADY HOSPITAL | 7/31/2007 | 8/2/2007 | GRADY HOSPITAL | 8/2/2007 | 17 |
| 99887746 | CERVICAL ALLOGRAFT TRAY | SCOTTISH HOSPITAL | 8/26/2007 | 8/28/2007 | NORTH FULTON HOSPITAL | 8/28/2007 | 18 |
| 99887746 | CERVICAL ALLOGRAFT TRAY | SCOTTISH HOSPITAL | 8/28/2007 | 8/30/2007 | NORTH FULTON HOSPITAL | 8/28/2007 | 18 |
| 99887746 | CERVICAL ALLOGRAFT TRAY | SCOTTISH HOSPITAL | 8/27/2007 | 8/29/2007 | NORTH FULTON HOSPITAL | 8/29/2007 | 18 |

FIG. 13

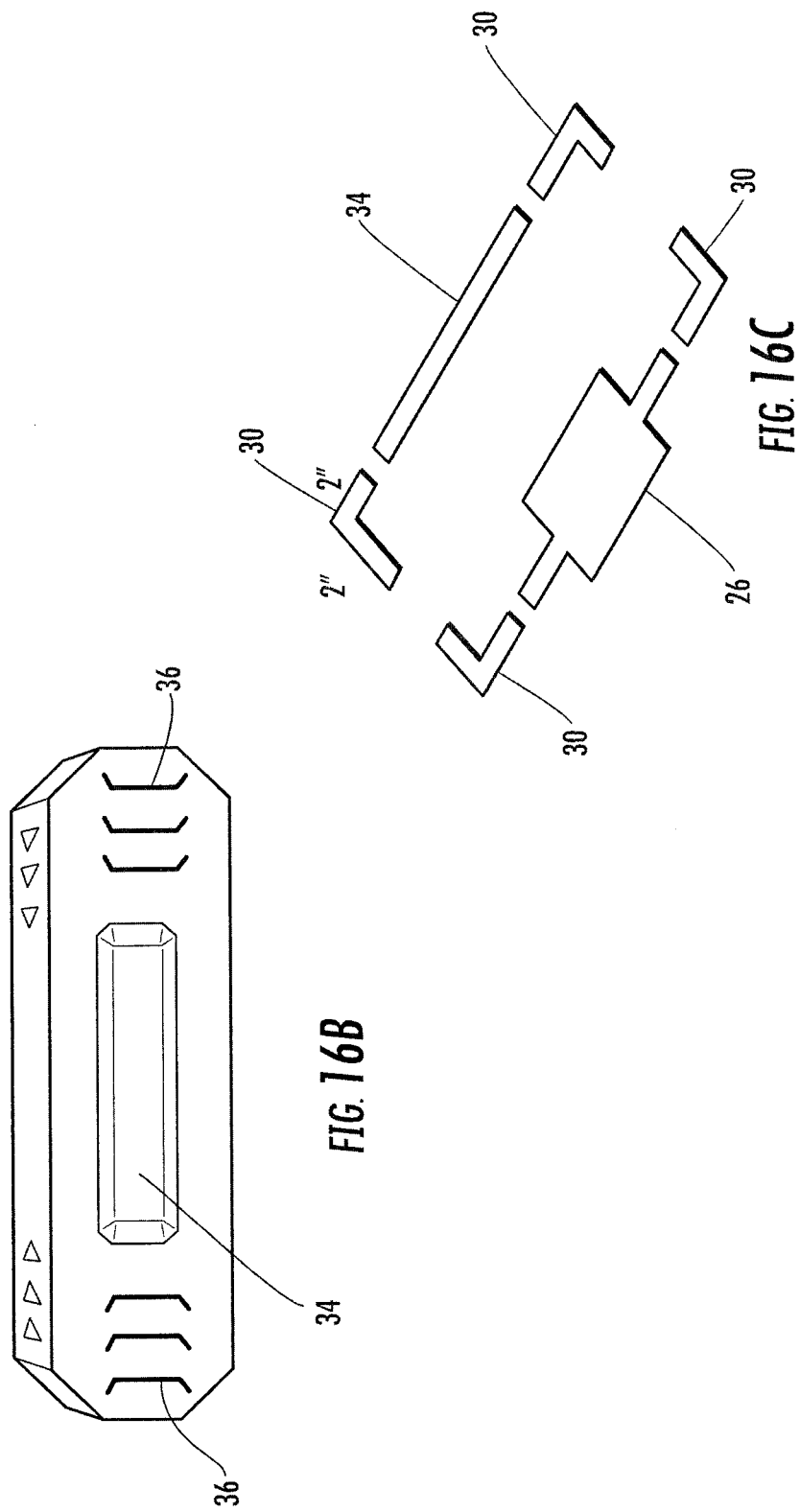

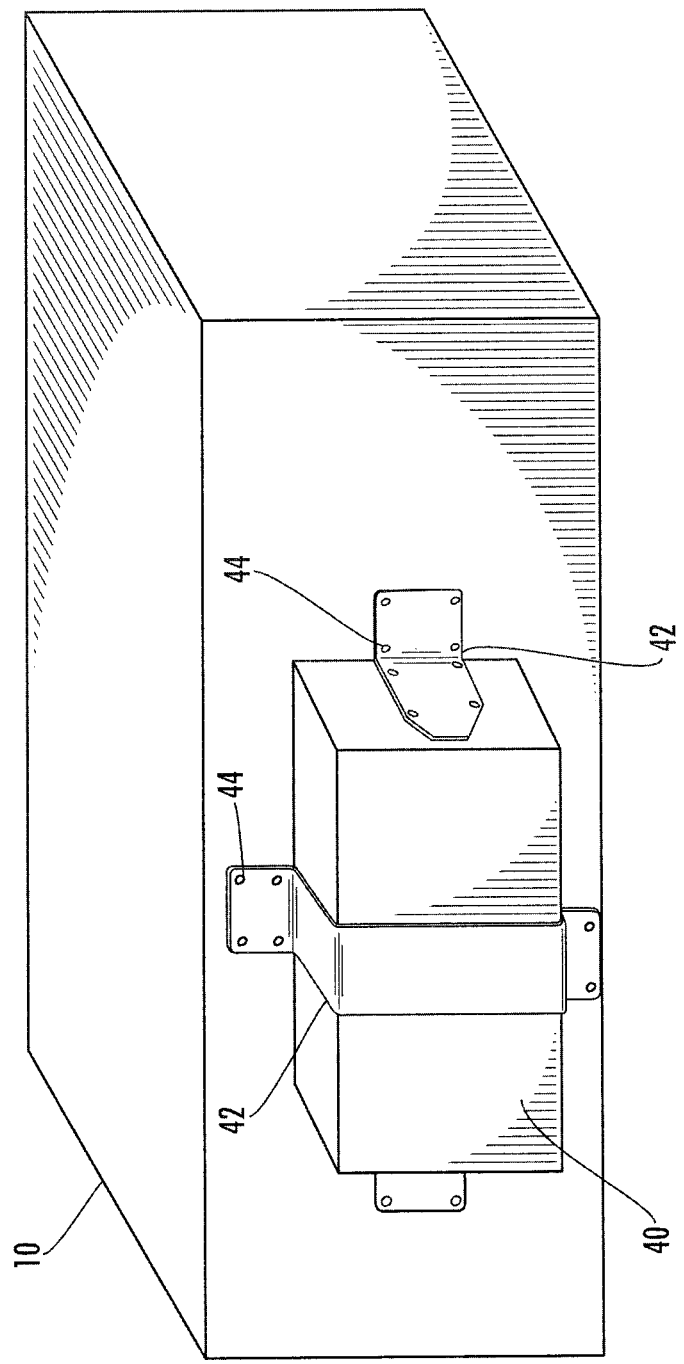

TRACKING SYSTEM AND DEVICE

CROSS REFERENCE TO RELATED APPLICATIONS

This application is a continuation-in-part of U.S. patent application Ser. No. 11/861,858, filed Sep. 26, 2007, now U.S. Pat. No. 7,868,754 entitled "MEDICAL SYSTEM AND TRACKING DEVICE", and U.S. patent application Ser. No. 12/963,309, filed Dec. 8, 2010, now abandoned entitled "MEDICAL SYSTEM AND TRACKING DEVICE", the entirety of these applications are incorporated herein by reference.

FIELD OF THE INVENTION

The present invention relates to supplies, supply containers, and in particular to an apparatus and system for tracking and locating these supply containers and their relative contents.

BACKGROUND OF THE INVENTION

Recent terrorist threats with means of using shipments as a way to deliver life threatening explosives has created concern for how a container can be shipped, and what the status of its relative contents might be during the shipment process. A supplier's container may be stolen and its respective contents may be tampered with along its shipping route. Current methods of tracking these containers, and their contents, present many dark zones or areas where traceability is not visible. A need for a more detailed level of accountability is now being required. It is for this reason that a real-time, true transparent method of tracking shipments from suppliers must be established.

These containers are subject to various methods of shipping. Because of this, the container and contents may be subject to different environmental pressures that could jeopardize or spoil the status of the shipment. Therefore, the contents, in some instances, may require a method of monitoring their temperature and exposures to the elements. When the items are shipped in the air by plane they may also have to abide by certain regulations such as those determined by the FAA (Federal Aviation Administration) including, but not limited to the tracking device powering down so that it does not attempt to send/receive signal transmission on its own or without proper protocol. In this instance the tracking device can use the altimeter sensor or barometric pressure portion of the device to signal the unit to enter into a dormant mode. Another method is to communicate directly through the airplane's wireless relay system, such as an onboard Wi-Fi router such as Gogo® Inflight Internet Wi-Fi service used to communicate the container's position and its overall status.

Another problem is excessive shipping. With the use of a real-time location tracking system, the inventory managers of the suppliers can use a system called "Radial Replenishment" where only inventory closest to the order's point of final destination is used to fulfill the order. By incorporating this method of inventory management, suppliers will spend less money on shipping, less resources will be exhausted, and less emissions from vehicles or airplanes will be expelled into the atmosphere.

Another problem is theft of the containers between the point of shipping origin and the final destination. Once the container is delivered to a shipping port and someone accepts shipment to forward to its next transient point, the container becomes the property and responsibility of the port authority. This creates a higher level of liability. There have also been instances of theft within the shipping ports. In some instances the containers have been shipped to the incorrect warehouse and this has not been discovered until the day delivery is expected. This shipping error will again result in postponement of the delivery and incur related expenses.

Therefore, what is needed in the art is a tracking device and system for tracking these containers and their respective contents from origination to the point of scheduled destination. This would enable the supplier's field representative to locate and monitor the container from the time it has left the point of origin until it arrived at the scheduled destination. The system is also capable of ordering additional supplies and billing for the use of the supplies and equipment.

DESCRIPTION OF THE PRIOR ART

U.S. Published Patent Application No. 2006/0017545 discloses a tracking system for monitoring the location of an object or a group of objects using RFID tags. These tags must be passed by an interrogator or tracking device to be detected. If the RFID devices are not within the range of the tracking devices, such an in a hospital store room, the tracking devices are unable to located the RFID devices. Some of these RFID tags can include a GPS feature to report their location. However, if the tags cannot communicate with the GPS satellites, such as when they are located within buildings, their location cannot be determined. Therefore, this system is not practical when tracking medical trays in hospitals.

U.S. Pat. No. 7,158,754, issued to Anderson and U.S. Pat. No. 7,158,030, issued to Chang, both disclose RFID tags which can be encapsulated on or attached to medical devices. These tags can only be tracked when they are passed by an interrogator or other tracking device. They cannot be located by tracking devices positioned outside of the building when they are within the building.

SUMMARY OF THE INVENTION

Briefly, the present invention is directed toward a tracking device and system for tracking supplies, in particular, containers and their components. The tracking device utilizes AGPS/GPS/GSM/CDMA/LTE/EVDO/TDMA technology to enable an individual to locate and monitor the movement of a container at any given time, and for any desired period of time. It may also use Wi-Fi to recognize the router's IP address to establish a location point of where the package may be. This is similarly portrayed in the software solution provided by Skyhook Wireless. The tracking system can also utilize virtual Geo-fences, a method of creating a perimeter of latitude and longitudinal points, to assist in determining the specific location of the containers relative to their destination points. Whenever a container passes one of these Geo-fences, the software recognizes it and information is sent to an individual or device monitoring the location of the container. Those directly related to the GeoFence will know what inventory may be within their perimeter and care for it accordingly. The tracking devices can also be activated by motion sensors to alert the tracking system of a possible theft of the container. The tracking system can also be programmed so the tracking device transmits its position at specific time intervals. The tracking device can also utilize other wireless communications such as Bluetooth, Zigbee, Rubee, RFID or Wi-Fi in order to determine a more specific location, such as a room within a building.

The tracking device is normally attached to a container in a manner such that only the individual who installed the tracking device, or the company providing the tracking service, can remove the tracking device. This prevents the tracking device from being removed from the container and left at a known location, such as the store room of a warehouse, while the contents are stolen. Normally the only time the tracking device may be removed from the container is to replace the batteries. The tracking device can also be equipped with a pager or beeper to assist in determining its precise location in large store rooms.

The tracking device is also weather/water proof and capable of withstanding elevated temperatures, such as those encountered in an autoclaving or in the cryogenic process. The tracking device may or may not include a shock, cold, heat, and moisture absorption insulation system to protect the device. The tracking device will also go through a power switch mode of operation to utilize the least amount of power necessary to transmit signals and information. This sequence will bring the unit to operate through several modes going from least power to most power based on signal transmission ability. The unit may also use various methods in order to charge the tracking device's power supply such as inductive charging, wireless radio frequency charging, or thermionic conversion which uses heat to recharge the battery. Additional methods of wireless recharging can also be used, such as solar panels or photovoltaic cells.

Accordingly, it is an objective of the instant invention to provide a system for tracking a container and its contents at all locations including inside of buildings.

It is a further objective of the instant invention to provide a tracking device which can withstand extreme temperatures.

It is yet another objective of the instant invention to provide a system for tracking shipments which includes information regarding the intended user of the shipment, the location at which the shipments are to be delivered and the representative of the shipper.

It is a still further objective of the invention to enable the containers to be ordered and shipped to the desired locations when required.

It is still a further objective of the instant invention to provide a tracking device which enables a determination of the status of the object being tracked.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 3 is a web page of the system illustrating an example through the scheduling of surgeries;

FIG. 7 is a web page for obtaining warehouse or hospital data;

FIG. 10 is a web page illustrating a schedule of surgeries or destinations for shipments to arrive;

FIG. 12 is a web page illustrating container or medical tray availability;

FIG. 13 is a web page illustrating inventory orders for products or medical trays;

FIG. 17 illustrates a third embodiment of a tracking device for a container or medical tray;

DETAILED DESCRIPTION OF THE INVENTION

Figure 1B:
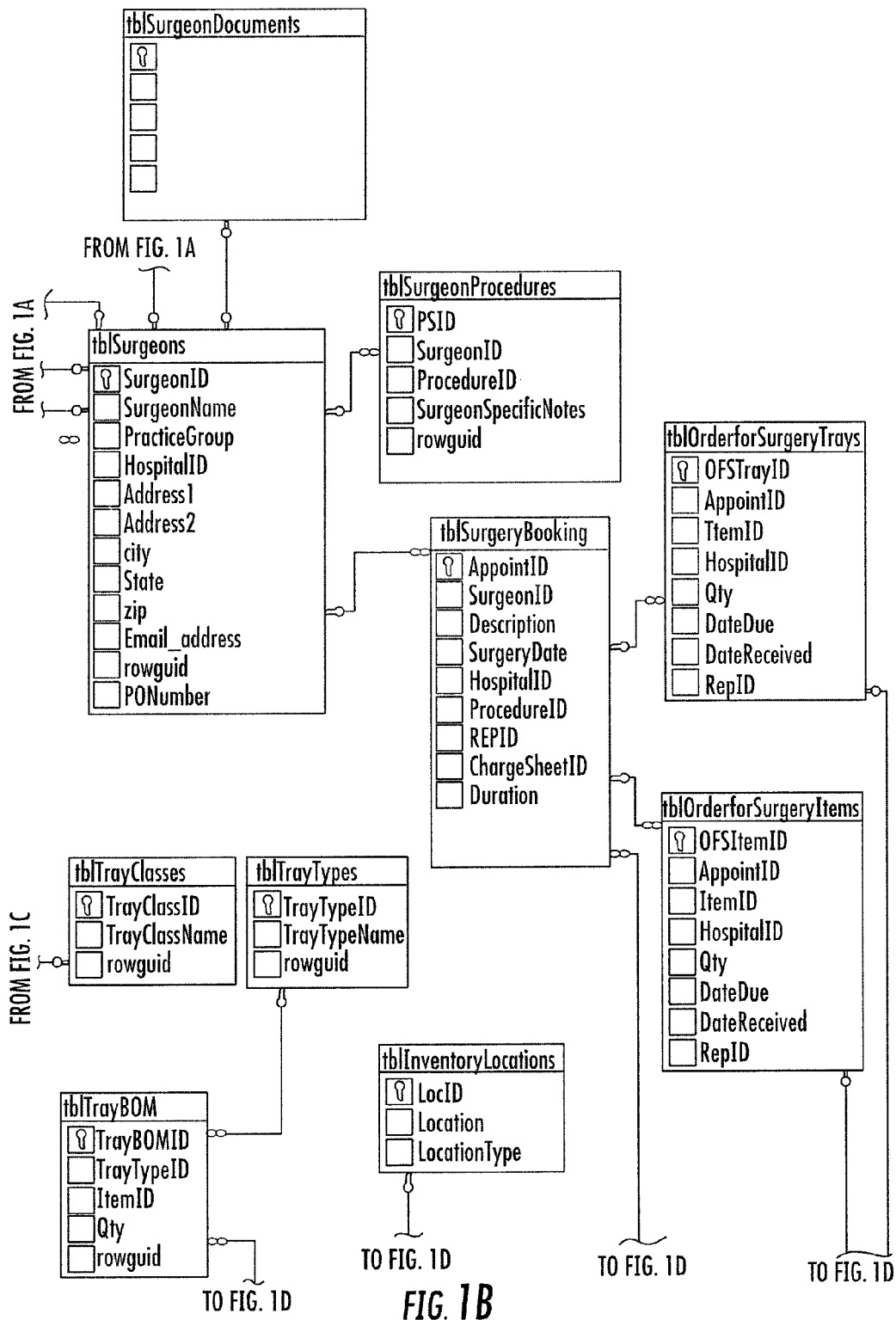
FIGS. 1 A-D are an overall flowchart of the various aspects of the device and how they are connected.

While the present invention is susceptible of embodiment in various forms, there is shown in the drawings and will hereinafter be described a presently preferred, albeit non limiting, embodiment with the understanding that the present disclosure is to be considered an exemplification of the present invention and is not intended to limit the invention to the specific embodiments illustrated.

A system and method for tracking an object, an article or an individual as it moves along a path is disclosed hereinafter. The system and method of the present invention do not require input from an individual whenever the object or article moves from one location to another. The system and method of the present invention do not require input from an individual to determine whenever the object or article's contents are removed from the container. A position indication device such as a Universal Mobile Telecommunications System (UMTS), AGPS (Assisted Global Positioning), Wi-Fi (IEEE 802.11), LTE (Long Term Evolution), CDMA (Code Division Multiple Access), RFID (Radio Frequency Identification) Interrogator, or Reader (Passive or Active), Rubee (IEEE P1902.1) Reader, Zigbee (IEEE 802.15.4) Reader or Gateway, Z-Wave Relay or Gateway, Wibree Transponder/Master, Bluetooth® Transponder/Master and/or GPS (Global Positioning System) device is attached directly to the article, container or object which is being tracked. A position indication device such as a Wibree Chip/Slave, Bluetooth Chip/Slave, RFID (Radio Frequency Identification) (Tag, Antenna, or Sensor)(Passive or Active), Rubee Tag (Tag, Antenna, or Sensor), Zigbee (Tag, Antenna, or Sensor), Z-Wave (Tag, Antenna, or Sensor) device is attached directly to or located in close proximity to the article, inventory item(s), container content(s), container, or object which is being tracked. Various types of GPS systems which are available for use include National Differential GPS System (NDGPS); Wide Area Augmentation System (WAAS); Continuously Operating Reference Station (CORS); Global Differential GPS (GDGPS) and International GNSS Service (IGS). Other types of position indicating devices may be used in place of the RFID (Radio Frequency Identification)(Passive or Active) or GPS devices. The positioning indicating device will transmit its location utilizing GPS (Global Positioning System), GSM (Global System for Mobile communications), CDMA (Code Division Multiple Access), LTE (Long Term Evolution), EVDO (Evolution Data Optimized), Wi-Fi (IEEE 802.11), WiMax (IEEE 802.16), TDMA (Time Division Multiple Access), or SMS (Short Message Service) technologies or a combination thereof. In addition, Relative Location Awareness (RLA) or an aircraft takeoff sensor can be employed.

The system is accessed through a web site or smartphone application wherein inventory personnel, port authorities, supplier's representatives, users, warehouse personnel and manufacturers can access information relating to the containers and their location. The containers and their contents can be ordered and transferred utilizing this web site. The costs of the containers and their contents can also be billed at this web site. For example, the information regarding the identification and location of the object being tracked can be transmitted to a cellular network tower using AGPS and then processed through a back end server. This information is then contained in a web-based platform and/or software.

Another embodiment of the present invention utilizes communicators which communicate with each other and other devices and transmit information regarding the identification and location of various objects being tracked. For example, a first communicator is preferably located in at least one object being tracked. The first communicator can be a RFID reader or utilize Bluetooth® communications. The first communicator can also be located in an autoclaveable enclosure. The first communicator communicates with a second communicator. The second communicator can be located in at least one object being tracked. The second communicator can include a pager, a beeper, etc. The second communicator can employ GPS, CDMA, GSM, LTE, TDMA and be SMS enabled. The second communicator can also be located in an autoclaveable enclosure. The second communicator further can communicate with a motion sensor. The second communicator communicates with a network or satellite to transmit information regarding the location and identification of the objects being tracked. A third communicator communicates with the first communicator. It provides the first communicator with information regarding the identification and location of the object being tracked. The third communicator can be an ID tag, a RFID tag or a Bluetooth® chip. Alternatively, the system can employ a fourth communicator. The fourth communicator can be Wi-Fi, Zigbee, Bluetooth® or a relay system.

In addition to the identification and location of the object being tracked, the present invention can indicate the status of the contents of the object/objects being tracked. For example, when the objects being tracked include many individual items, the present invention can determine if all of the items which were initially shipped are still in the container or if some have been removed, altered, broken, etc. The system of the present invention is also ISN Band Airport and healthcare environment compliant.

Figure 1C:
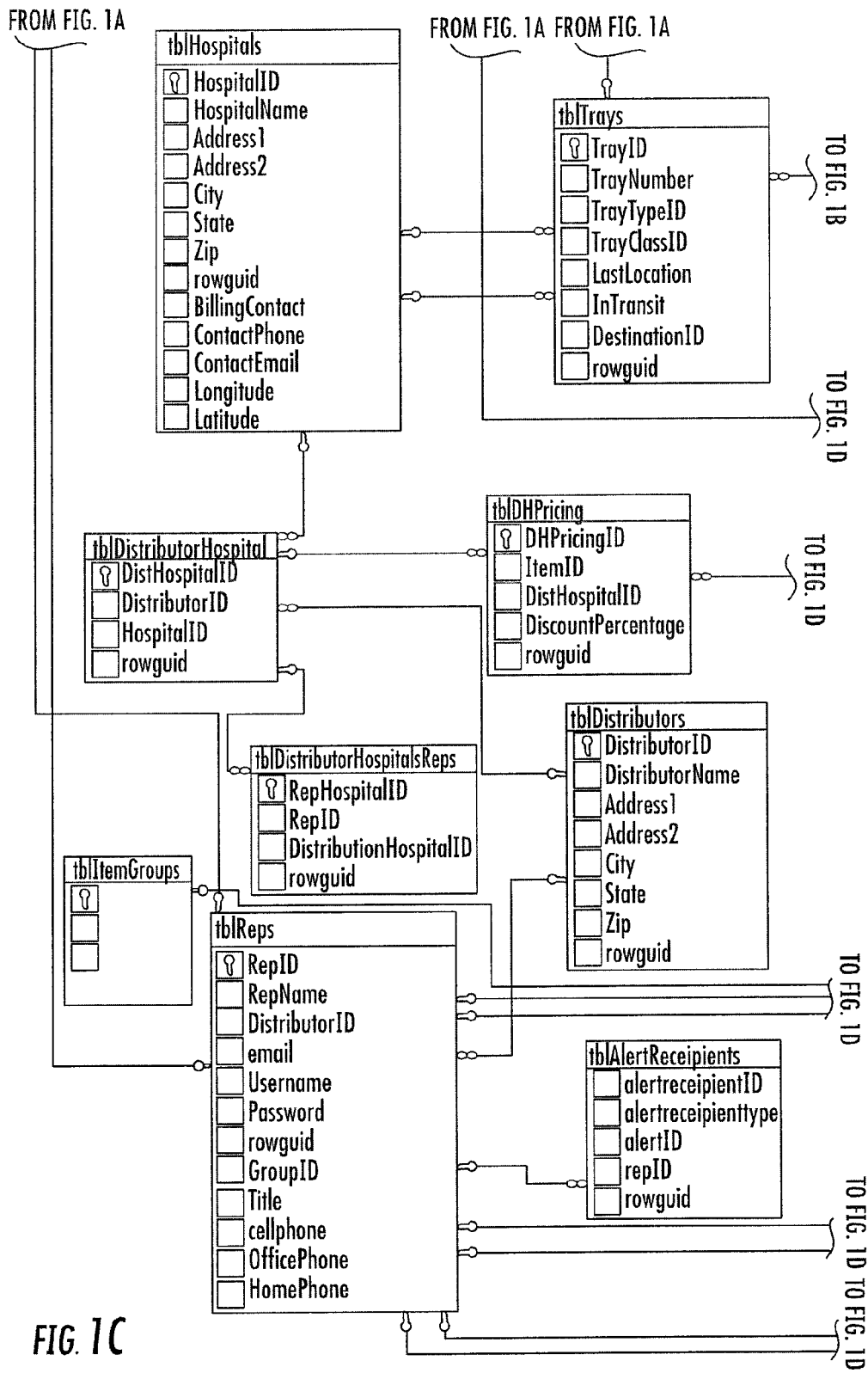
Figure 1D:
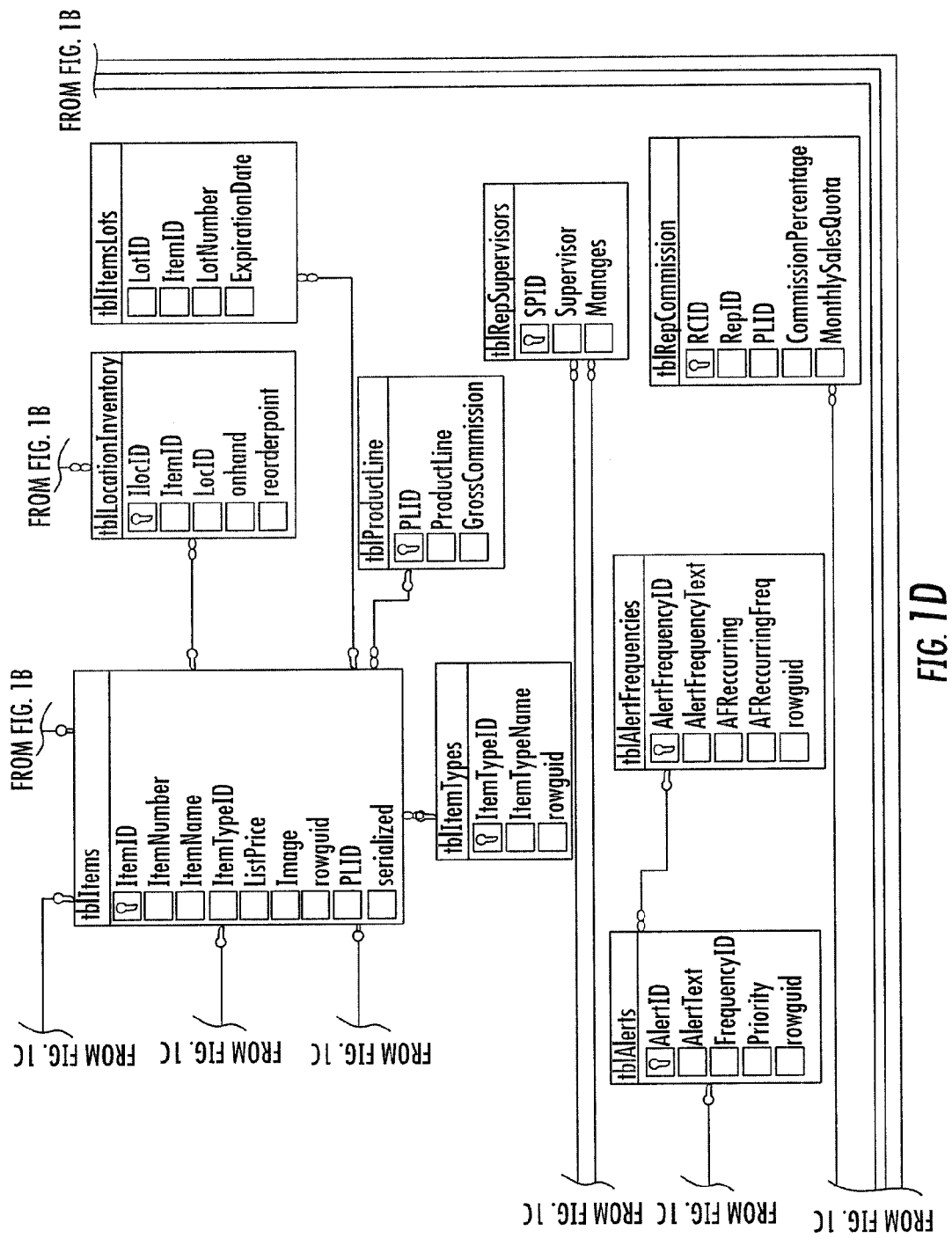

FIGS. 1 A-D illustrates how the various menus are linked to each other so that the supplier's reps can access all the information pertaining to the trays and the orders in which they are to be used. The various menus illustrated in FIGS. 1 A-D include examples using a medical illustration of how this functions, the Rep Surgeons, the Surgeon Family Members, the Surgeon Phones, the Surgeon Documents, the Surgeon Hospital Affiliations, the Charge Detail Sheet, the Charge Sheet Header, the Surgeons, the Surgeon Procedures, the Order for Surgery Containers, the Rep Procedures, the Container Location Tracking, the Surgery Booking, the Hospitals, the Containers, the Container Classes, the Container Types, the Inventory Locations, the Order for Surgery Items, the Container Bill of Material, the Distributor or Hospital, the DH Pricing, the Items, the Location Inventory, the Item Lots, the Product Line, the Distributor Hospitals Reps, the Distributors, the Item Types, the Item Groups, the Reps, the Alert Recipients, the Alerts, the Alert Frequencies, the Rep Supervisors and the Rep Commission.

Figure 2B:
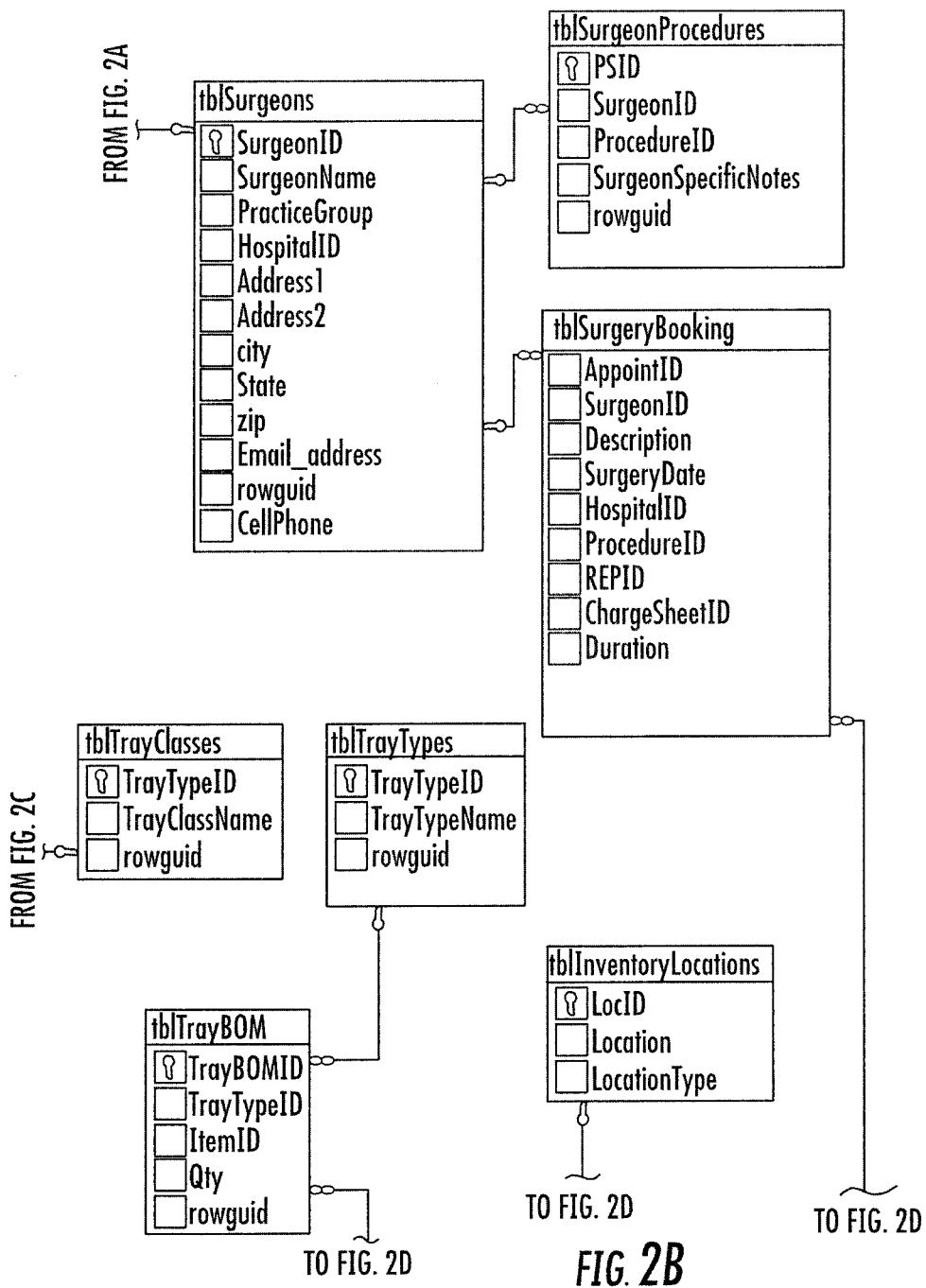
FIGS. 2 A-D are a flowchart similar to FIGS. 1 A-D with some additional information.
Figure 2C:
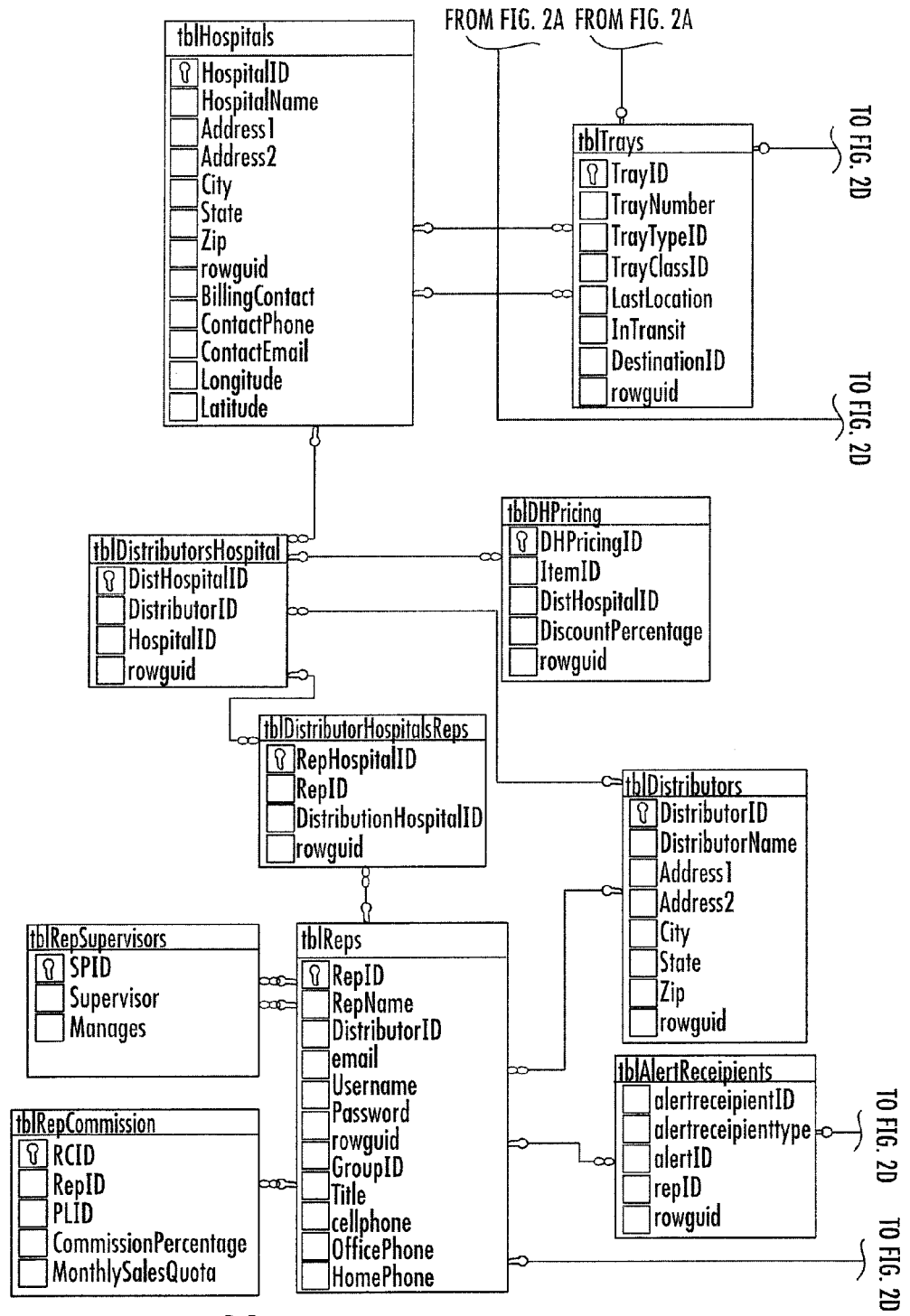
Figure 2D:
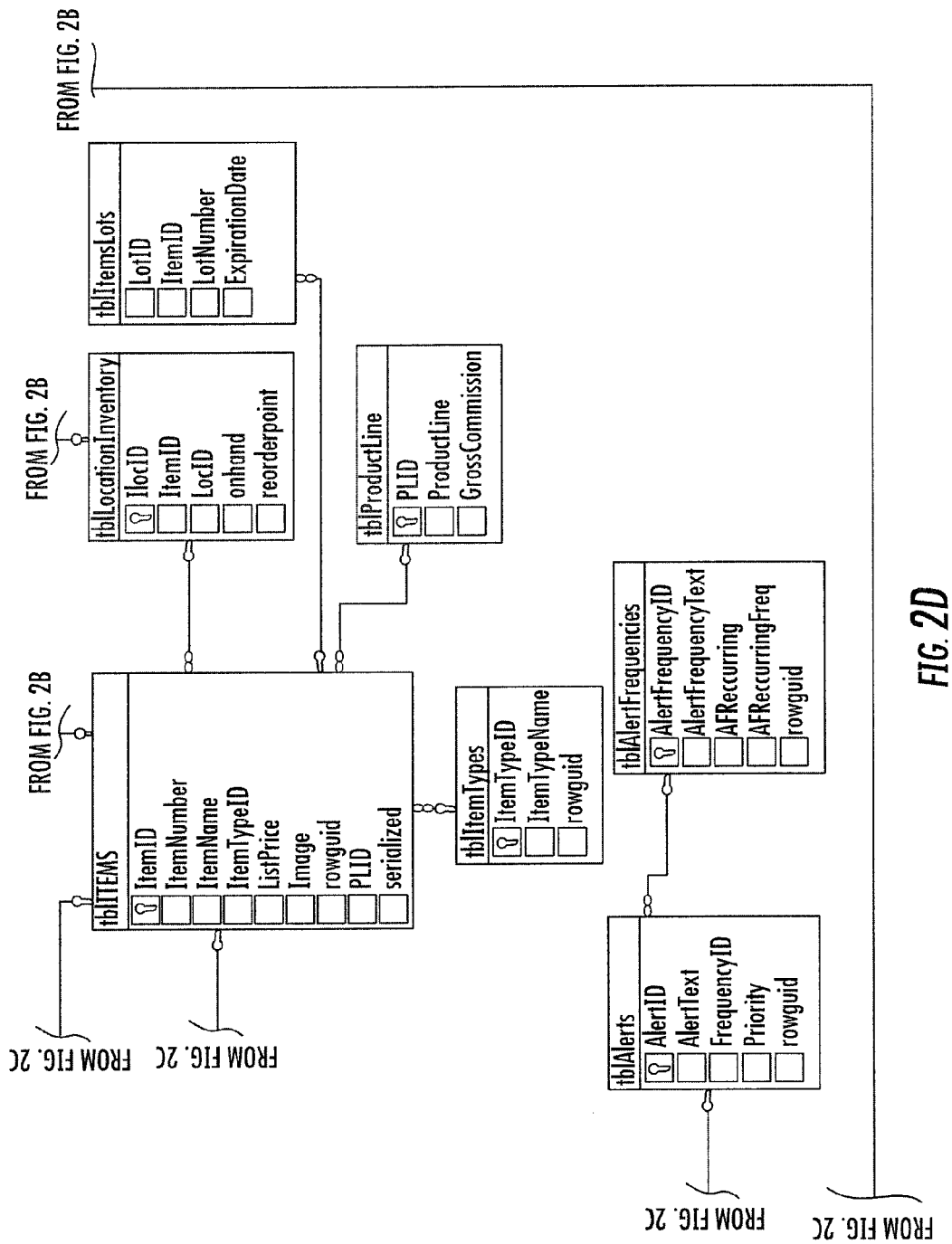

FIGS. 2 A-D also illustrate how various menus are linked to each other so that the medical device reps can access all the information pertaining to the Containers and the surgical procedures in which they are to be used. The various menus illustrated in FIGS. 2 A-D include the Charge Sheet Detail, the Charge Sheet Header, the Surgeons, the Surgeon Procedures, the Surgery Booking, the Container Location Tracking, the Hospitals, the Containers, the Container Classes, the Container Types, the Inventory Locations, the Container Bill of Materials, the Distributor Hospital, the DH Pricing, the Items, the Location Inventory, the Item Lots, the Product Line, the Distributor Hospital Reps, the Distributors, the Item Types, the Rep Supervisors, the Reps, the Alert Recipients, the Alerts, the Alert Frequencies and the Rep Commission.

Figure 3:
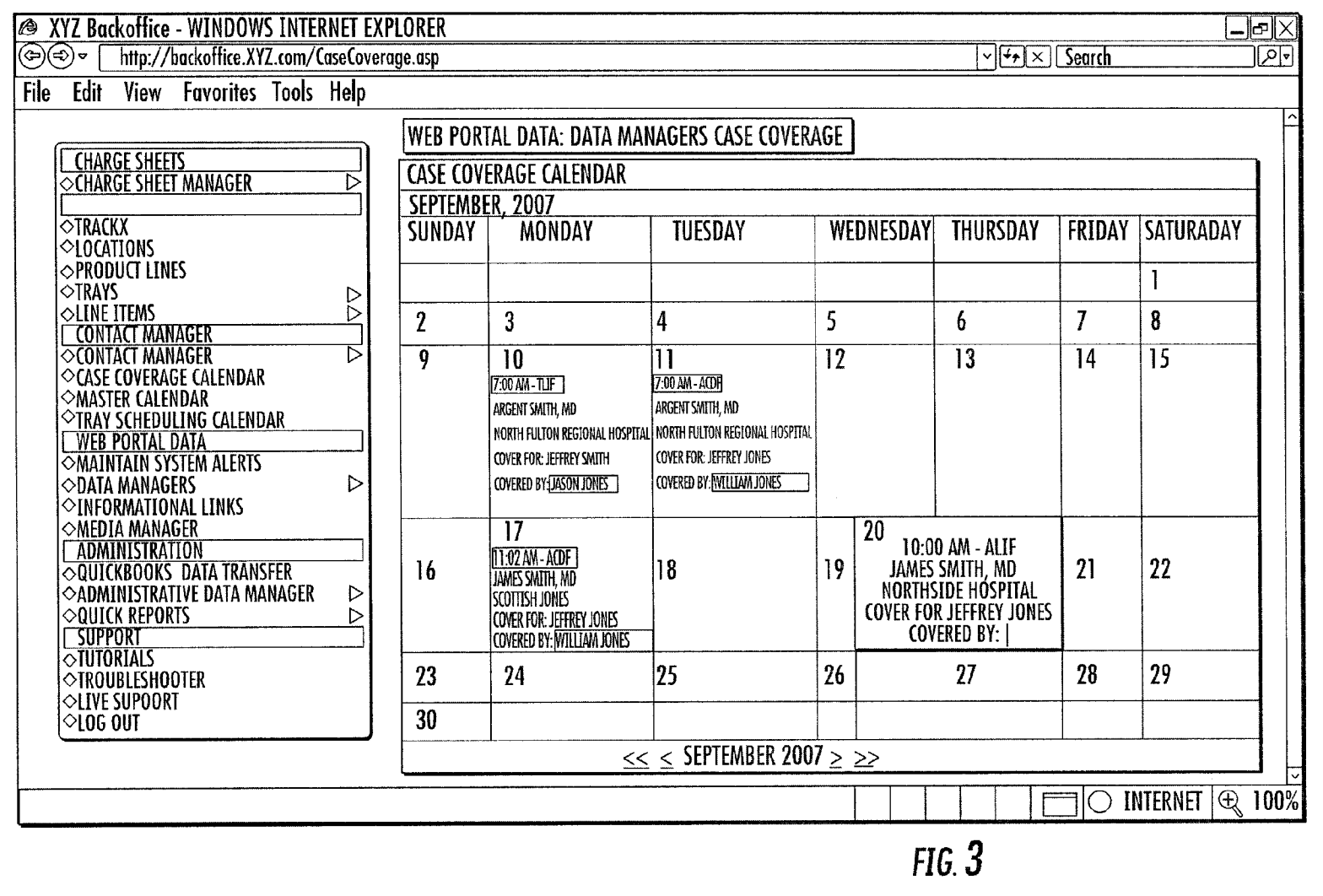

An example of the surgical case coverage for different surgical procedures is illustrated in FIG. 3. For example, on Monday, Sep. 10, 2007, the time and type of the procedure is listed at the top, 7:00 AM—TLIF. Next, the name of the surgeon is listed, Argent Agrawal. Next, the hospital where the procedure is being done is listed, North Fulton Regional Hospital. Next, the name of the medial device representative present at the procedure is listed, Jeffery Smith. Finally, if the medical device representative is not available, his replacement is listed, Jason Graves. The charge sheet menu appears in all of the web pages. This enables the user to quickly access the information that he or she is seeking.

Figure 4:
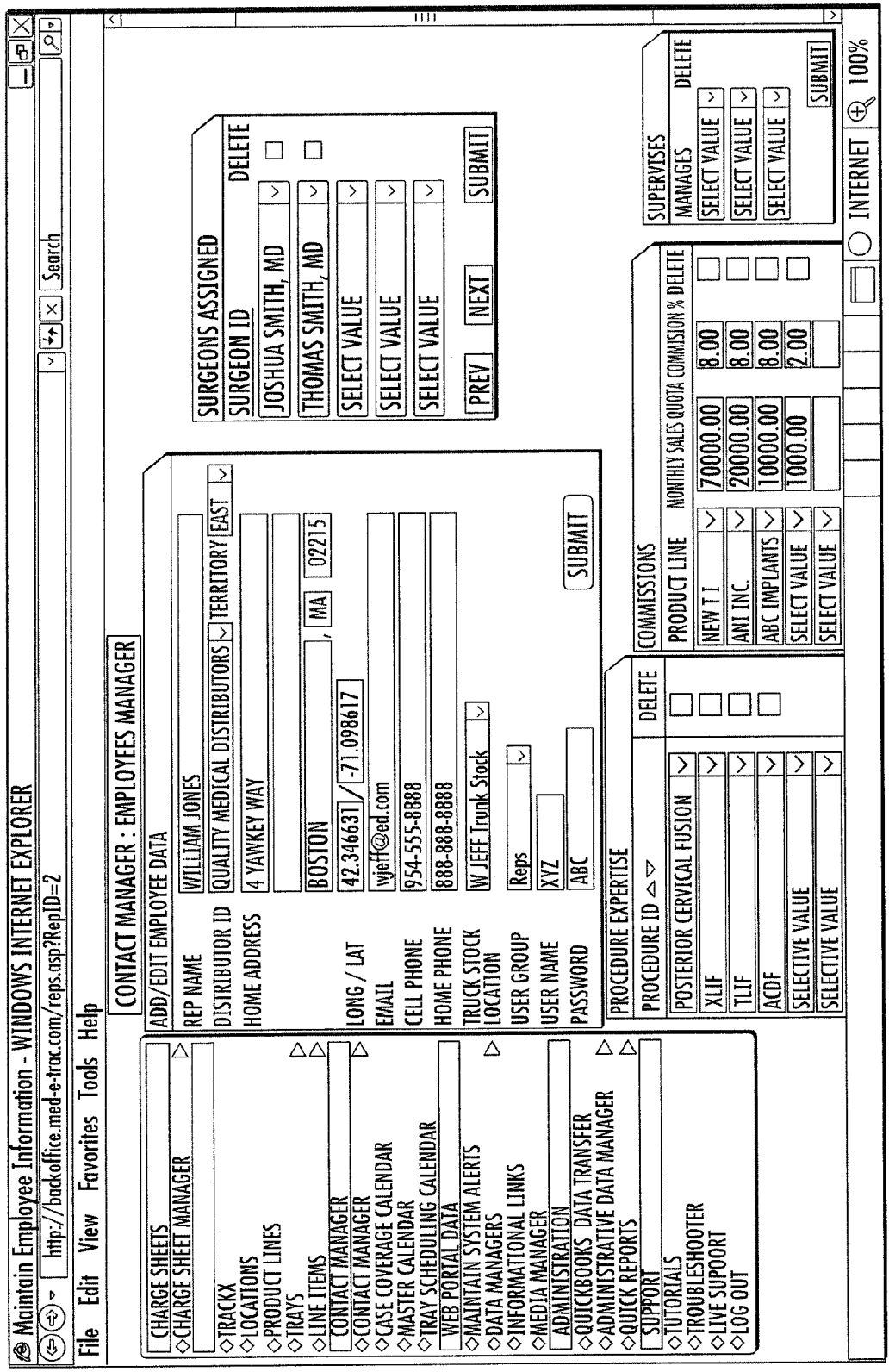
FIG. 4 is a web page of the system illustrating how data is entered regarding suppliers or medical devices representatives.

An example of the information with respect to each surgical representative is illustrated in FIG. 4. The representative's personal information is available including how he can be contacted. The surgeons he is assigned to are also illustrated. The surgical procedures in which he has an expertise are listed. His commissions for the use of various medical devices are listed. Finally, all personnel that he supervises are also listed.

Figure 5:
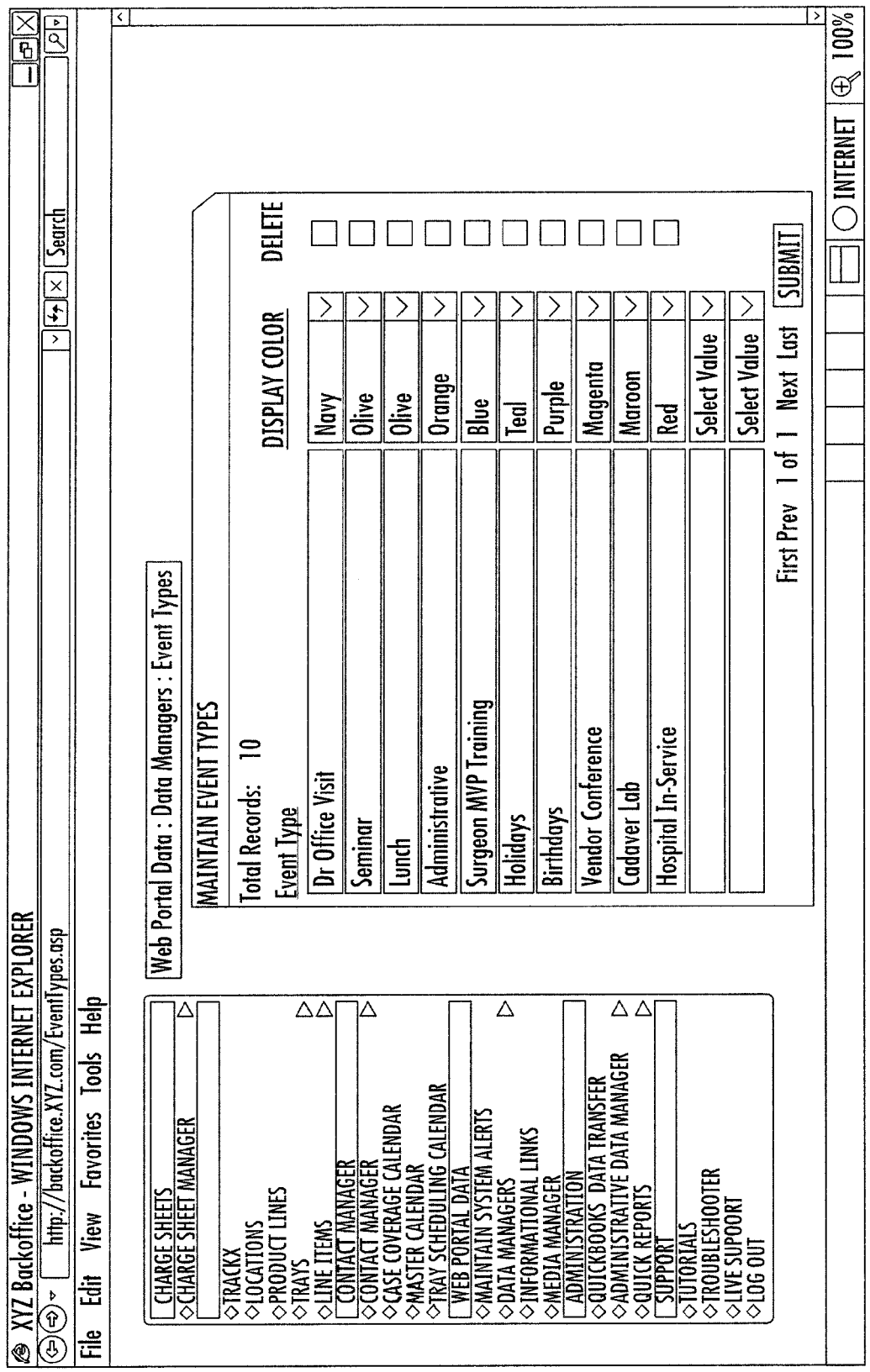
FIG. 5 is a web page illustrating the color codes on the charge sheet.
Figure 6:
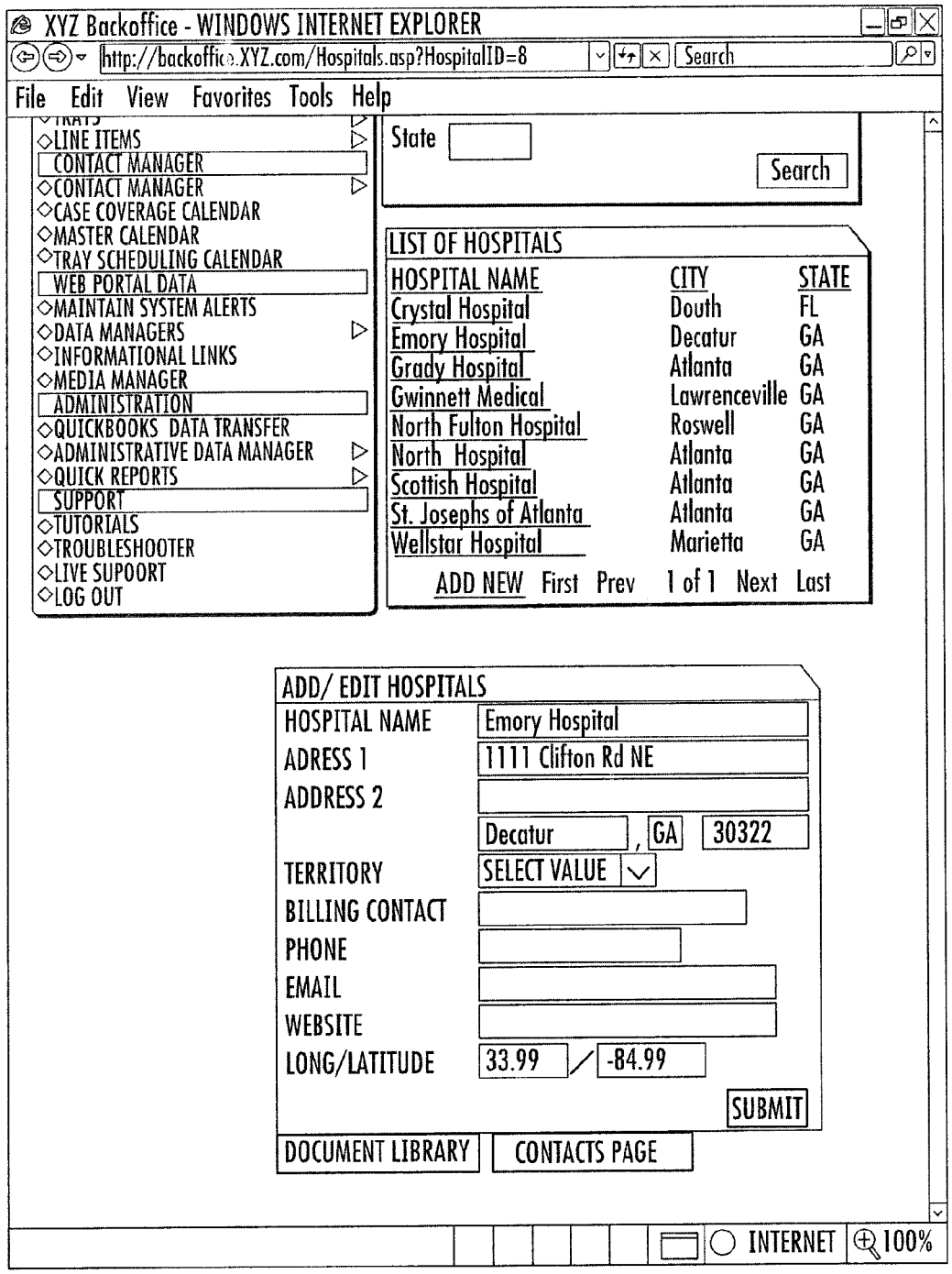
FIG. 6 is a web page for entering warehouse or hospital data.
Figure 7:
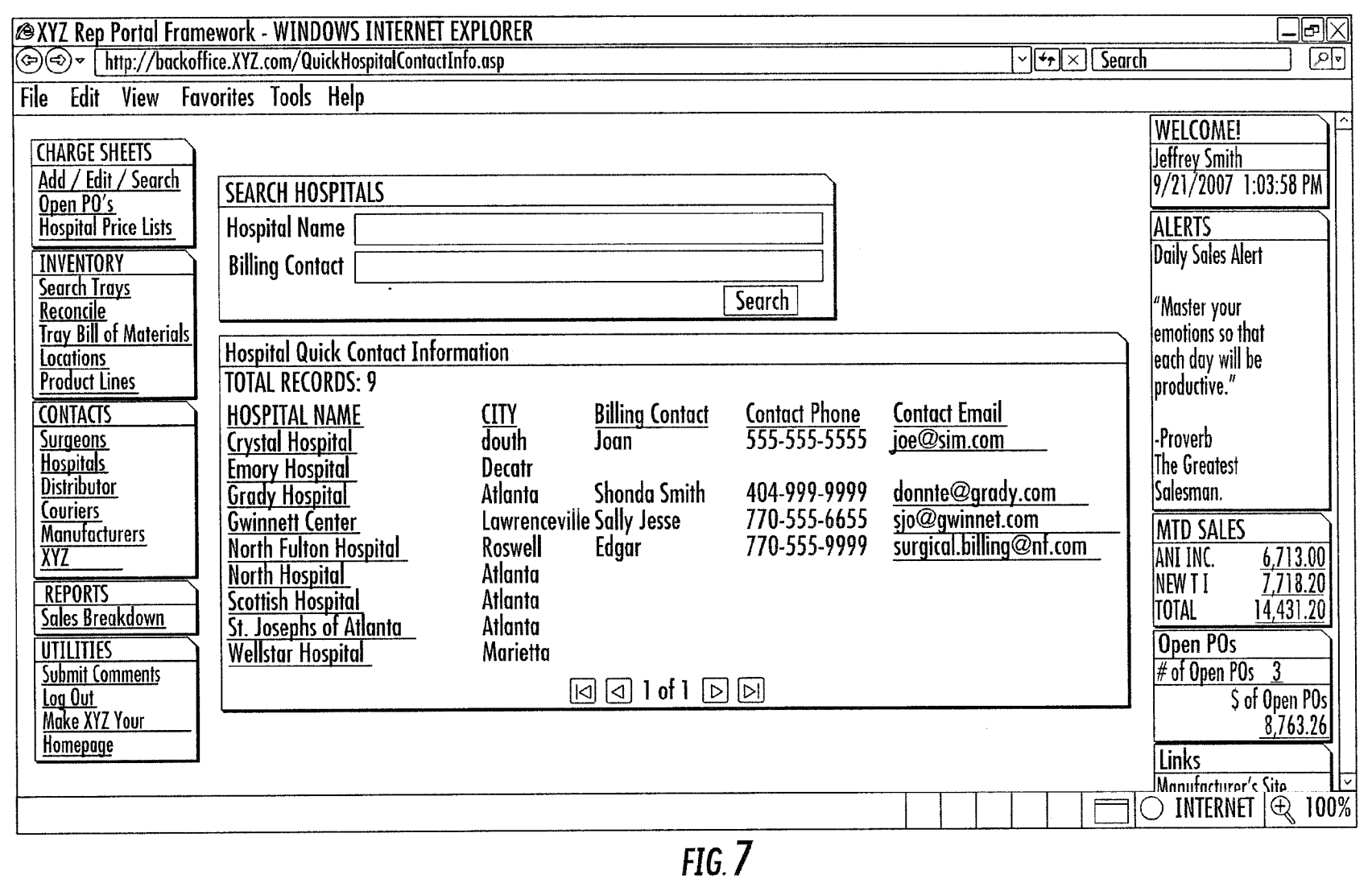

FIG. 5 is a menu of the various colors which are assigned to various events. For example, doctor visits are navy, Surgeon training is blue and hospital in-service is red. These colors are utilized in the case coverage illustrated in FIG. 3. Hospital information is illustrated in FIG. 6. A list of the hospitals which utilize the medical Containers is provided. When a particular hospital is selected, the address and location of the hospital is provided. Also, information regarding billing is provided. Another method of accessing hospital information is illustrated in FIG. 7. The hospital or billing contact can be searched in the system. This web page also includes a quick contact information list.

Figure 8:
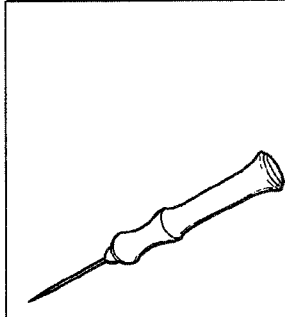
FIG. 8 is a web page illustrating container, content, or medical device information.

The contents of the various medical Containers are illustrated in the web page in FIG. 8. A description of each of the items including a photograph, the procedure in which they are used, the cost of the items and the manufacturer are readily available. An inventory of the various Containers is also available. Utilizing this information, the surgical representative can familiarize himself or herself with the contents of each Container prior to the surgical procedure.

Figure 9:
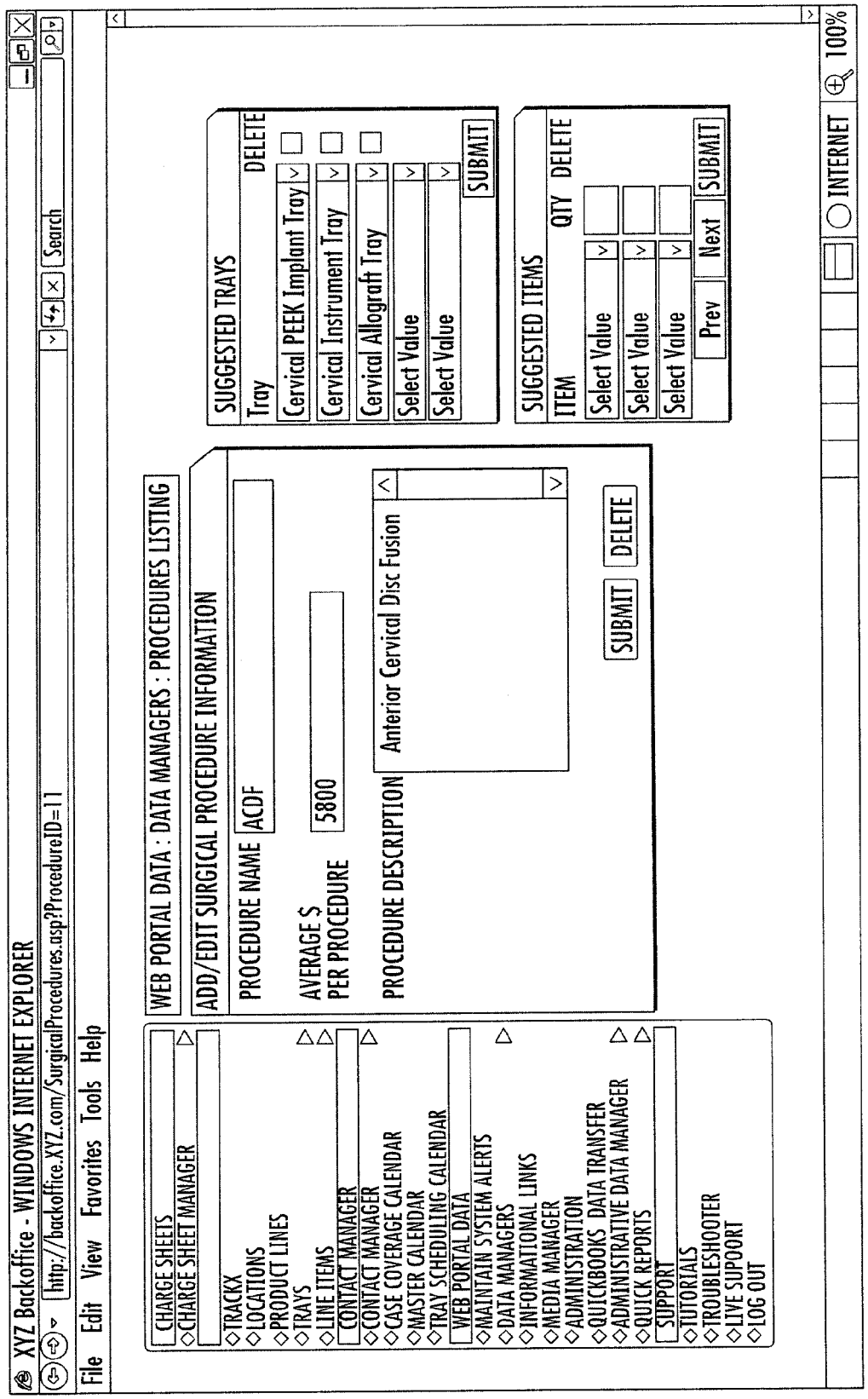
FIG. 9 is a web page for entering surgical procedure or delivery information.

The information with respect to different surgical procedures and the medical Containers required for the procedures is illustrated in FIG. 9. The representative can select the various Containers which the surgeon will need or has requested for the procedure. This information is submitted to the system to indicate the availability of the Containers, and if certain Containers and their respective contents must be supplied from other locations. If this is the case, then an order is placed and the required Container is shipped to the desired location.

Figure 10:
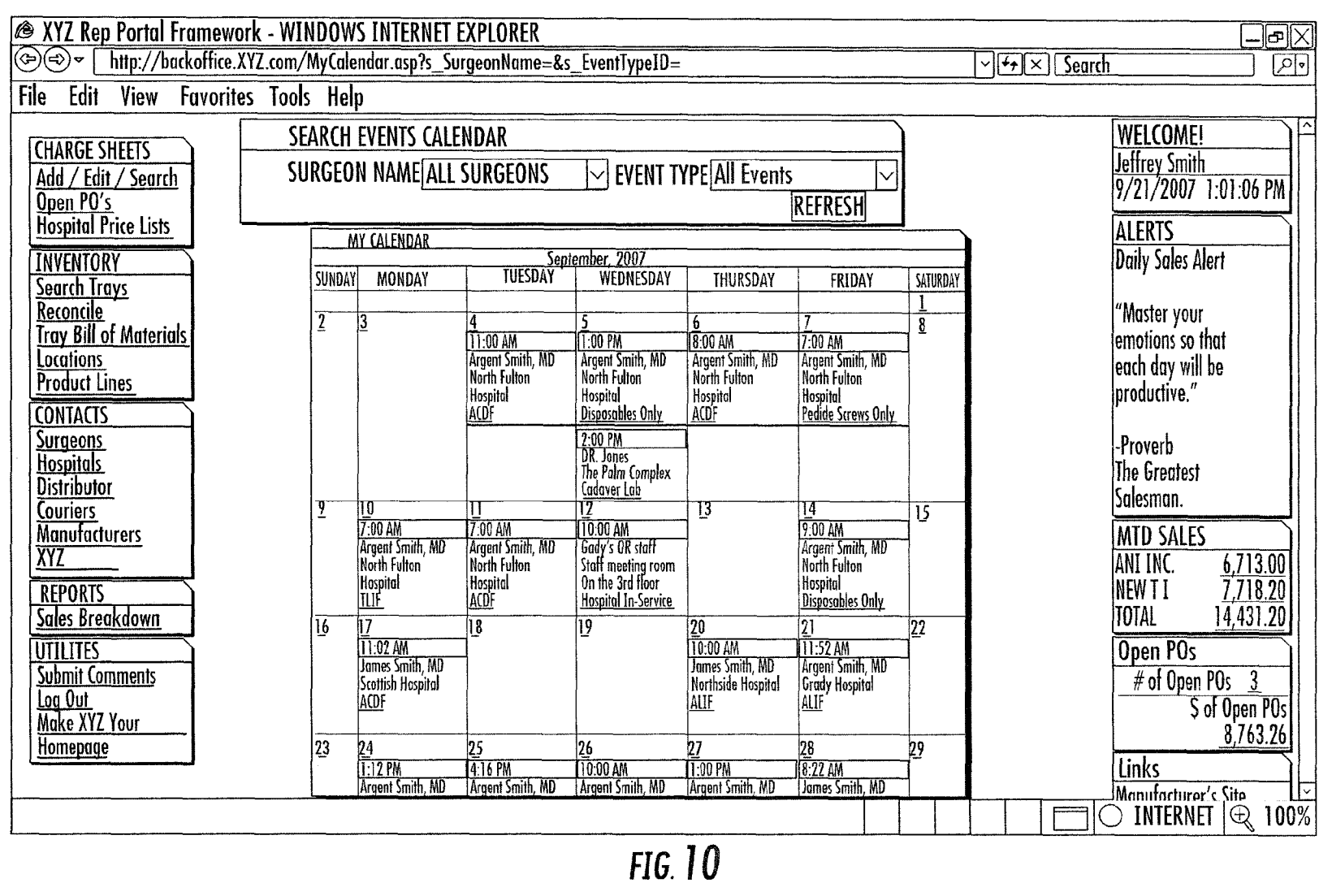
Figure 11:
FIG. 11 is a web page illustrating supplier's client or surgeon's information.

FIG. 10 illustrates a medical representative's calendar. His surgeries and other activities are on the calendar. He can also access his sales information, track the medical inventory, and access information with respect to his contacts. All of this can be done wherever he has access to the Internet. An example of the information regarding specific surgeons is illustrated in FIG. 11. With this information he is better equipped to establish a working relationship with the surgeon. Should the representative need information regarding specific Container, he can also access this as illustrated in FIG. 12. This information includes an identification of the Containers, the location of the Containers, information regarding a hospital at which the Container is required, the date on which the Container is to arrive at the hospital, the date of the surgery and the date the Container will be available again if it is not needed for the surgery.

Figure 13:
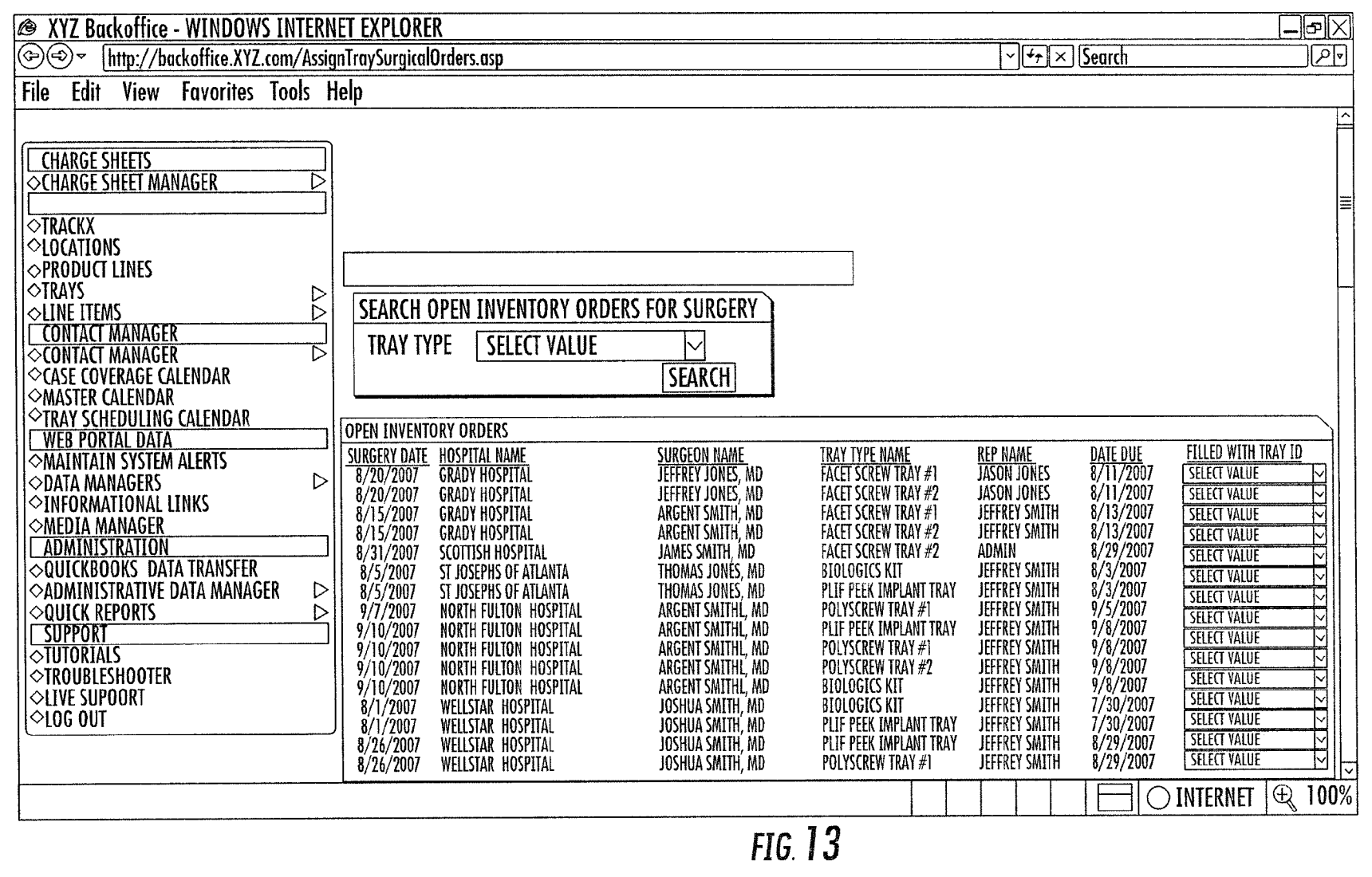
Figure 14:
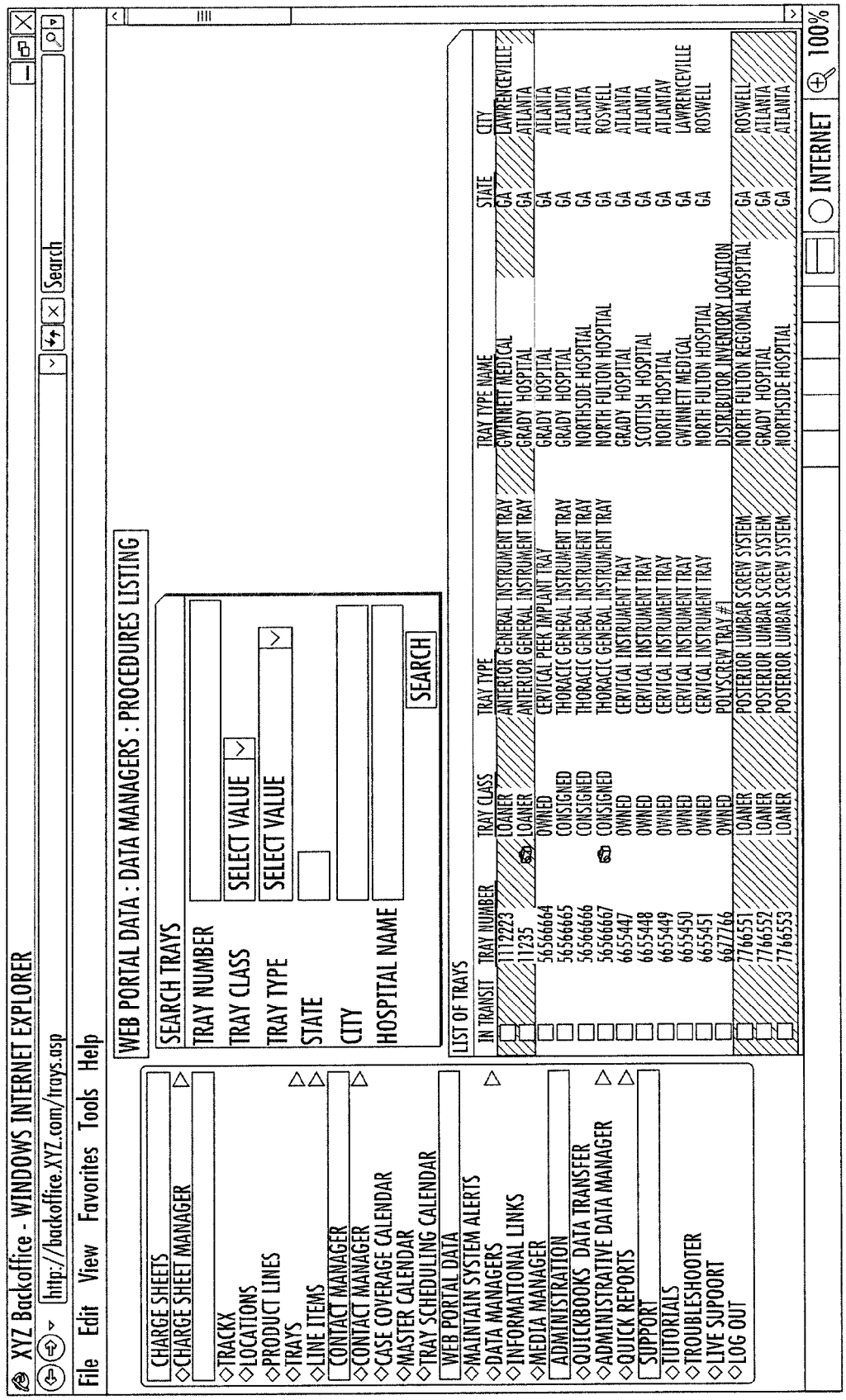
FIG. 14 is a web page illustrating the location of product containers or medical trays.

An inventory of Container orders is illustrated in FIG. 13. The date of the surgery, the surgeon's name, the specific Container required, the hospital and the representative's name assigned to the Container are provided. The representative can then locate an appropriate Container and assign it to the surgery. A list of the Containers available is illustrated in FIG. 14. This information lists the specific Container, the location of the Container, if the Container has already been purchased by the hospital and any special notes regarding the Container. The notes are indicated by an icon next to the Container class.

Figure 15C:
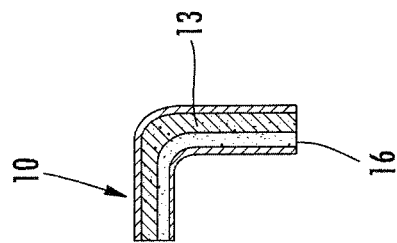
FIGS. 15 A-C illustrates an embodiment of a tracking device for a container or medical tray.
Figure 15B:
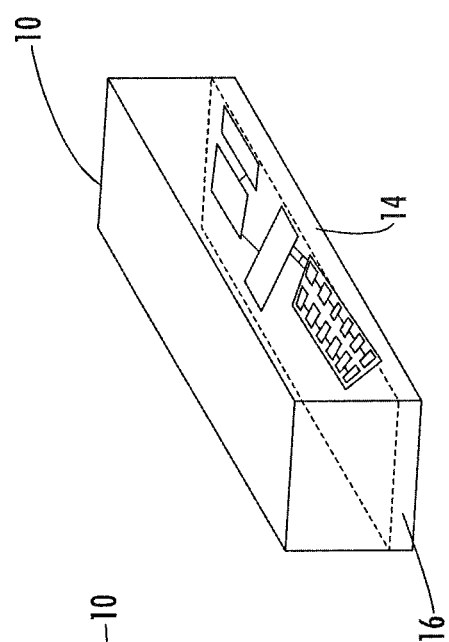
Figure 15A:
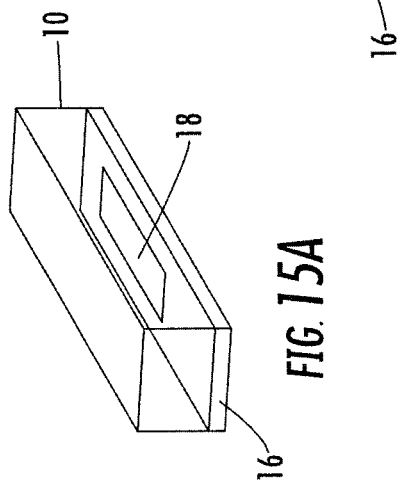
Figure 16A:
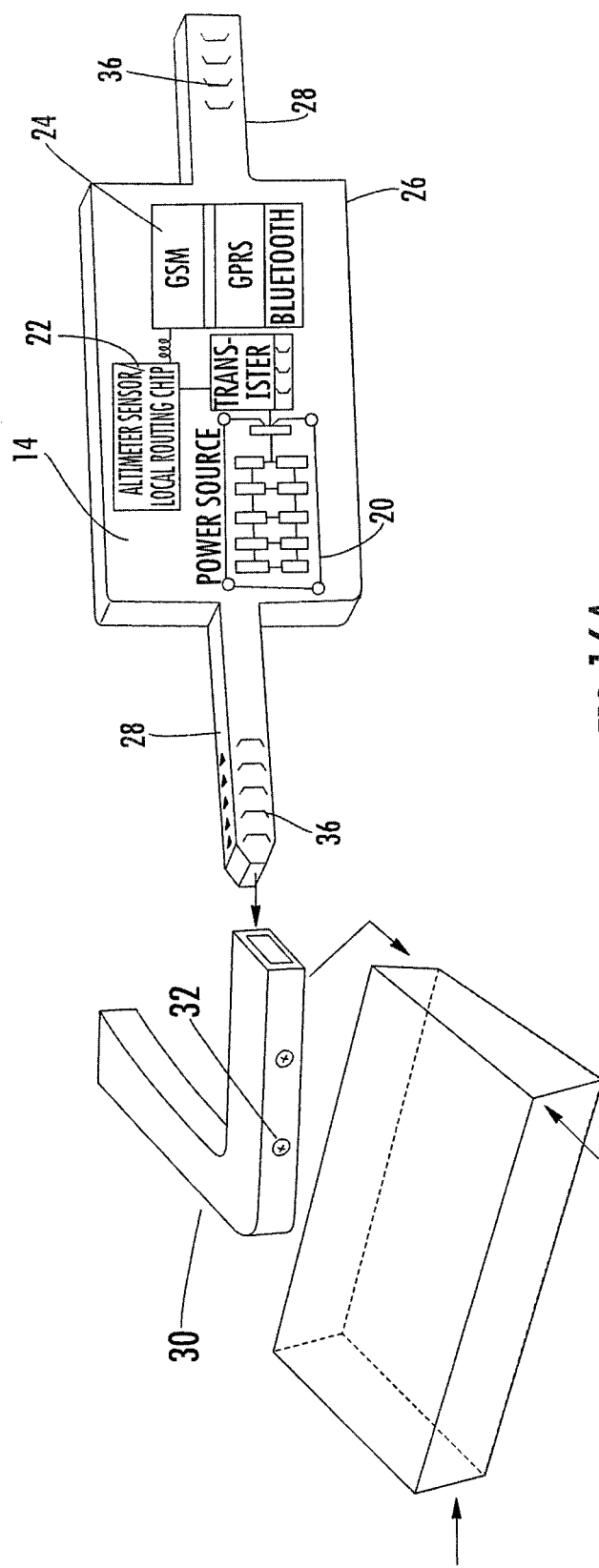
FIGS. 16 A-C illustrates a second embodiment of a tracking device for a container or medical tray.

Various tracking devices for the Containers are illustrated in FIGS. 15-17. In FIGS. 15A and 15B illustrate a first embodiment of the present invention wherein the Container of the present invention is indicated as 10. The Container normally comprises a closed box. The contents (not shown) are arranged within the Container to insure proper placement. The tracking device Container is preferably composed of a stainless steel or polymer based exterior 13 and has a similar interior. Other materials with the desired properties could also be utilized. The tracking device 14 is located in the lower portion or attached to the body of the Container, FIG. 15B. The tracking device is placed in the lower portion, in a false bottom, or attached to the undercarriage of the Container in a enclosure composed of a stainless steel or polymer based exterior insulated with a foam or syntactic microballoon glass woven quilted material incorporating a phase changing material (PCM) 16. The foam functions as both an insulator and a shock absorption device. The Containers are normally sterilized at temperatures above 270° F. or cryogenically frozen at temperatures below −240° F., and the insulator helps protect the tracking device from these extreme temperatures. Sterilization of the containers or objects within the containers can be accomplished utilizing wet or dry heat, chemicals or radiation. Once the tracking device is placed in the Container 10, an access door 18 is secured in a manner that prohibits unauthorized personnel from accessing the tracking device. The access door is preferably provided with a waterproof and extreme temperature resistant seal, preferably a hermetic seal or gasket ring (not shown). The access door is used for battery replacement in the power source. The foam can be a syntactic microballoon glass woven quilted material or a PCM (Phase Change Material). The tracking device 14, as illustrated, in a second embodiment of the present invention, in FIG. 16A, comprises a power source 20, a motion sensor 22, and a communicator 24 which utilizes AGPS, GSM, GPRS, CDMA, SMS, Wi-Fi and/or Bluetooth® to communicate the location of the Container. An individual seeking the location of the container can establish contact with the tracking device with their mobile phone, web-based device such as an Ipad®, tablet PC, laptop computer, desktop computer or second transceiver. The tracking device will then indicate the location of the container. This type of communication system permits the tracking of containers inside of buildings where GPS devices will not function. The individual's mobile communication device, or another external communication device, can be programmed through the system's software to ping the tracking device at regular intervals. This helps conserve the batteries in the power supply of the tracking device. The location ping will also utilize the tracking device's technology in the most power efficient sequence, which is usually a method of utilizing the short range solution first, and then the long-range solution if transmission is hindered. An example of this would be that the unit would first use the less power consuming Wi-Fi or Bluetooth® network established in the building to send/receive the location signal; if that is not possible, it can then use GPS. If that is not possible, it can then use cellular triangulation to establish location, connectivity, and transfer of information to its respective user. In some cases a motion sensor 22 can trigger the second communicator 24 whenever the container is moved.

Objects which can be tracked include, but are not limited to, medications, medical devices, patients, batteries, implants, coolers, produce items, weapons, animals, boxes, cylinders, Pelican™ cases, a chest, submarines, assault vehicles, jewels, pallets, luggage, cabinets, money bags, airplanes, helicopters, vehicles, boats, tanks, thermometers, works of art, safes, toolboxes, computer systems, servers, freight containers, motorcycles, shopping carts, sleeping monitors, heart monitors, oxygenators, vials, vacutainer bottles, film containers, engines, construction equipment, mobile armories, trains, etc. Some of the objects being tracked are powered. They can receive their power from photovoltaic cells, a wireless radio frequency method, a kinetic charging method, an inductive charging method, a switched-mode powering method or a Thermionic conversion method.

The ultimate user of the device being tracked is normally concerned with the location of the device and the approximate time or arrival of the device. This is especially important to hospital personal, surgeons, and doctors. It is also important to inventory managers, police officers, pilots, military agents, jewelers, baggage handlers, etc.

A second embodiment of the tracking device is illustrated in FIGS. 16 A-C. This tracking device is secured around the outer periphery of the Container. This is known as the "Halo" design. The tracking device is located in the main element 26 of the device. The tracking device includes a motion sensor or altimeter 22, a power supply 20, an inductive charging mechanism and a first communicator, a second, third, and fourth communicator 24. An access door or panel (not shown) provides access to the tracking device to enable battery replacement or other operations. The access door may be secured by a keyed or keyless lock, and cannot be readily accessed by unauthorized personnel, and is normally located on the rear side of the main element 26. The main element 26 is provided with legs or extensions 28. These legs connect to corner elements 30. The legs are secured to the corner elements utilizing rivets or other fasteners 32. A connection member 34 secures corner elements together, as illustrated in FIG. 16C. The corner elements 30 are designed to connect to each other when they are secured to any sized Container. Connection members 34 can also be utilized to connect corner elements 30 to each other whenever the width of the medical Container is larger than normal. A connection member 34 is illustrated in FIG. 16B. The connection member 34 is provided with zip-tie-like one way connectors 36 at both ends of the connection member. These connectors allow the connection member to be inserted into the corner elements but not withdrawn therefrom. After these elements have been connected to each other, additional fasteners such as rivets 32 are also used to secure the elements together. Connectors 36 are also provided on the main element 26 as illustrated in FIG. 16A. The Container can be formed from the same material as the Container of the embodiment of FIGS. 15 A-C. Protective foam can also be utilized in the main element to protect the tracking device.

A third embodiment of the tracking device is illustrated in FIG. 17. The tracking device is positioned in a housing 40 which is secured to an outer portion of a Container 10. Straps 42 secure the housing 40 to the Container. Rivets 44 or similar fasteners such as keyed or keyless locks secure the straps 42 to the Container. The fasteners are designed so they are not removable by unauthorized personnel. An access door or panel (not shown) provides access to the interior of housing 40 for battery replacement or access to the tracking device. A handle 46 can be provided on the Container to assist in transporting the Container. The Container is formed from the same material as the Container of the embodiment of FIGS. 15 A-C. Protective foam can also be utilized in the housing 40 to protect the tracking device.

Figure 18:
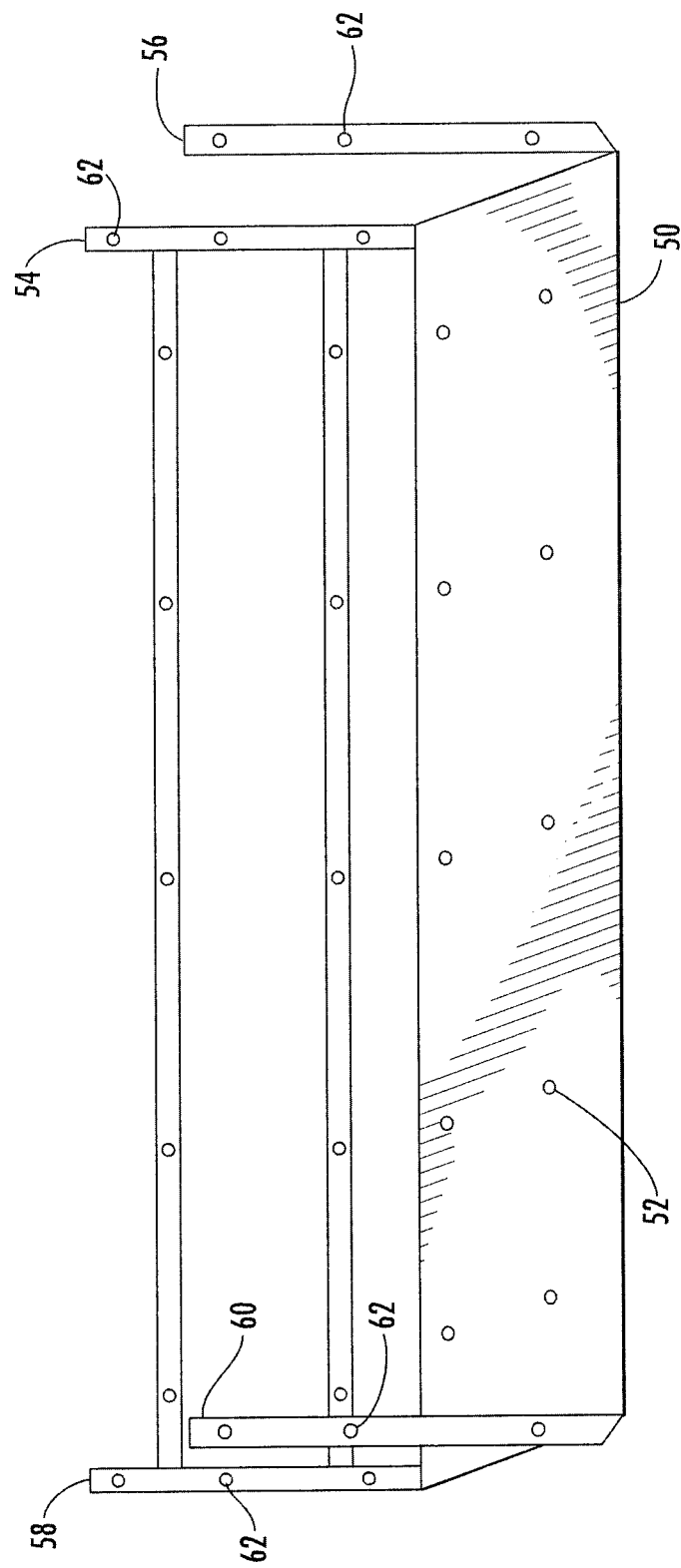
FIG. 18 illustrates a fourth embodiment of a tracking device for a container or medical tray.

A fourth embodiment of the tracking device is illustrated in FIG. 18. This is known as the "Exoskeleton" design. The Container 50 can be formed from the same material as the Container of the first embodiment. The tracking device is positioned in the housing 50 which is attached to the internal or external portion of the container. The corner portions of the device 54-60 contain sensory antenna contact points 62 which detect the contents of the container. Externally, these antennas transmit through a radio frequency transferable material. If the items are removed, the tracking device (second communicator) is notified via the first communicator of the present status. This information is then transferred via the fourth or second communicator to the web-based software's interface for the user to identify the container's status of its contents.

Figure 19:
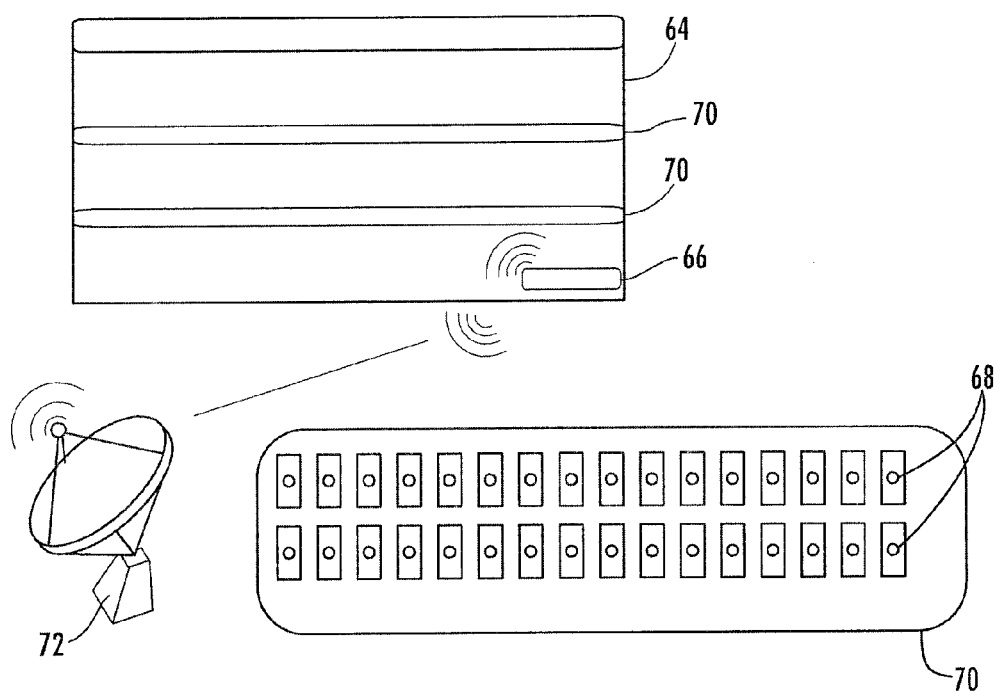
FIG. 19 illustrates a fifth embodiment of a tracking device for a container or medical tray.

A fifth embodiment of the tracking device is illustrated in FIG. 19. This is known as the "Compartment" design. The Container 64 can be formed from the same material as the Container of the first embodiment. The tracking unit 66 connects to a separate piece that houses the antennas for the units. The embodiment of the smaller separate enclosure is made of a protective material that allows the antennas to transmit signals through. The tracking device is positioned in the container 64 which is attached to the internal or external portion of the container. Inside of the container each item has an assigned location 68 within a tray 70. When the item is removed from its assigned location, the first communicator is notified and transmits the information through the fourth or second communicator 72 in order to notify the user of the container's inventory status. There is a transmission barrier between the locations 68 within the trays so that one location 68 does not pick up the information transmitted from an adjacent location and transmit it to the tracking unit. This would result in duplicate information being transmitted.

Figure 20:
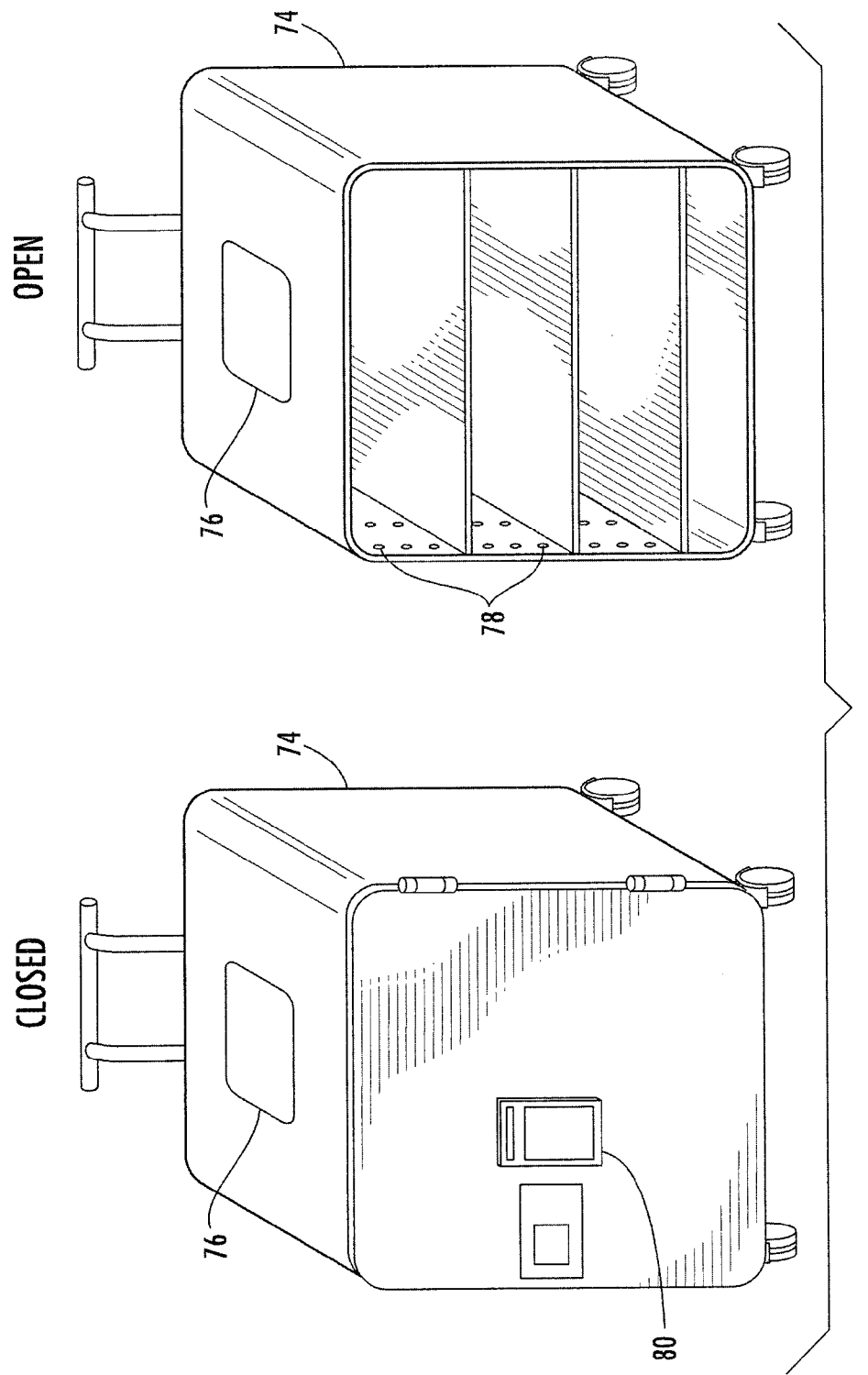
FIG. 20 illustrates a sixth embodiment of a tracking device for a container or medical tray.

A sixth embodiment of the tracking device is illustrated in FIG. 20. This is known as the "Mobile Vendor" design. The tracking device 76 is positioned in the uppermost portion of the container housing 74. Inside of the container, various antennas 78 are placed to recognize tagged items (third communicator). On the front of the door of the enclosure is a lock 80 which can be keyed or keyless. This lock is connected with a wire or wirelessly to the tracking device 76 in the uppermost portion of the container. When the door has opened and an item is removed, the tracking device will report its inventory status once the door is closed and the lock is in the closed or sealed position. The tracking device's fourth or second communicator receives this information from the first communicator which is monitoring the status of the third communicator(s). The lock will assist in identifying which user opened the door and at what time.

Figure 21:
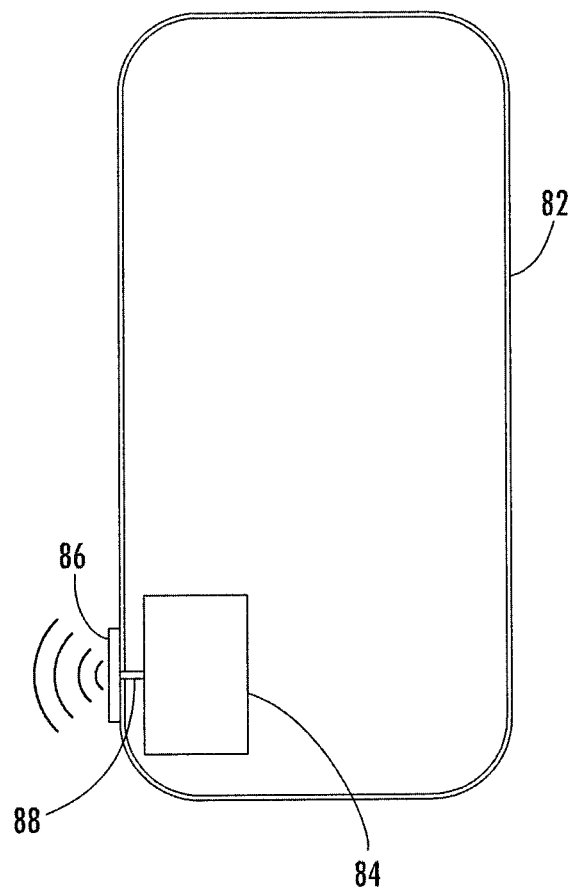
FIG. 21 illustrates an embodiment of a tracking device wherein the container does not permit the transmission of signal therethrough.

FIG. 21 illustrates a container 82 made of stainless steel or other materials which do not permit the transmission of signals therethrough. Therefore, the tracking unit 84 is located within the container to receive information regarding the objects being tracked which are located within the container. The tracking unit 84 is connected to an external antenna 86 via a hard wire connection 88 which passes through the container 82.

Figure 22:
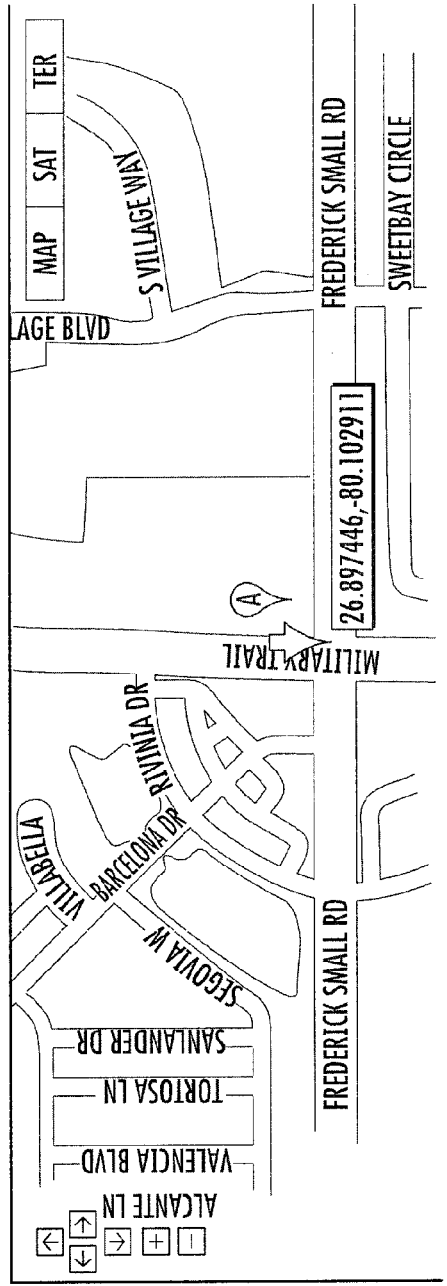
FIG. 22 illustrates the software that can be used with the tracking device.

FIG. 22 is a screen shot of the software which can be used in conjunction with the tracking device of the present invention to locate the object being tracked.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:
1. A system for tracking shipped objects comprising:
    a container for containing at least one object to be tracked;
    a third communicator within said container and secured proximate to each object to be tracked within said container and associated with said object, each said third communicator including electronic information regarding said associated object to be tracked;

a first communicator within said container for selectively reading said electronic information from each said third communicator, said electronic information accumulated in a memory of said first communicator, said first communicator in electronic communication with a second communicator positioned within said container;

said second communicator constructed and arranged to receive said electronic information regarding each said object to be tracked from said first communicator, said second communicator being constructed and arranged to transfer said electronic information from within said container over a long distance network upon request, whereby said information regarding each object to be tracked can be viewed from a remote location.

2. The system for tracking shipped objects of claim 1 wherein said system further includes a fourth communicator, said fourth communicator constructed and arranged to receive said electronic information regarding each said object to be tracked from said first communicator, said second communicator being constructed and arranged to transfer said electronic information over a short distance network upon request, whereby said information regarding each object to be tracked can be viewed from a remote location.

3. The system for tracking shipped objects of claim 1 wherein said second communicator includes a motion detector for detecting motion of said container, whereby said second communicator aggregates said electronic information from each said third communicator regarding each said object to be tracked, said electronic information automatically transferred via said long distance network to a predetermined receiver for viewing.

4. The system for tracking shipped objects of claim 1 wherein said third communicator is a radio frequency identification device.

5. The system for tracking shipped objects of claim 1 wherein said third communicator is a Bluetooth device.

6. The system for tracking shipped objects of claim 1 wherein said second communicator includes a global positioning system, said global positioning system constructed and arranged to provide a global position along with said electronic information regarding each said object to be tracked.

7. The system for tracking shipped objects of claim 1 wherein said second communicator utilizes cell technology for said data transfer.

8. The system for tracking shipped objects of claim 2 wherein said fourth communicator is a wi-fi device.

9. The system for tracking shipped objects of claim 2 wherein said fourth communicator is a Zigbee enabled device.

10. The system of claim 1 wherein said electronic information regarding said at least one object to be tracked from said second communicator is transmitted to a cellular network tower using CDMA and processed through a back end server, which information is later contained in a web-based platform.

11. The tracking device of claim 1 wherein a protective insulation to extreme temperatures is provided adjacent said transmitting device.

* * * * *